United States Patent [19]

Levitt

[11] 4,453,971

[45] Jun. 12, 1984

[54] HERBICIDAL SULFONAMIDES

[75] Inventor: George Levitt, Wilmington, Del.

[73] Assignee: E. I. Du Pont de Nemours and Company, Wilmington, Del.

[21] Appl. No.: 421,414

[22] Filed: Sep. 22, 1982

Related U.S. Application Data

[60] Division of Ser. No. 242,581, Mar. 11, 1981, Pat. No. 4,369,058, which is a continuation-in-part of Ser. No. 142,436, Apr. 21, 1980, abandoned, which is a division of Ser. No. 955,504, Oct. 27, 1978, Pat. No. 4,225,337, which is a continuation-in-part of Ser. No. 937,552, Sep. 1, 1978, abandoned, which is a continuation-in-part of Ser. No. 840,168, Oct. 6, 1977, abandoned.

[51] Int. Cl.³ .................. C07D 251/46; C07D 251/18; A01N 43/66

[52] U.S. Cl. ........................................ 71/93; 544/113; 544/211; 544/212

[58] Field of Search ...................... 544/211, 212, 113; 71/93

[56] References Cited

FOREIGN PATENT DOCUMENTS 1515 4/1979 European Pat. Off. ............ 544/211

Primary Examiner—John M. Ford

[57] ABSTRACT

N-(heterocyclicaminocarbonyl)arylsulfonamides, such as 3-isocyanato-N-[(4-methoxy-6-methyl-1,3,5-triazin-2-yl)aminocarbonyl]benzenesulfonamide or methyl [3-[[(4-methoxy-6-methylpyrimidin-2-yl)aminocarbonyl]aminosulfonyl]phenyl]carbamate, are useful for the regulation of plant growth and as herbicides.

18 Claims, No Drawings

HERBICIDAL SULFONAMIDES

RELATED APPLICATIONS

This is a division, of application Ser. No. 242,581, filed Mar. 11, 1981 now U.S. Pat. No. 4,369,058, which is a continuation-in-part of U.S. Ser. No. 142,436 filed Apr. 21, 1980, now abandoned, which is a divisional of U.S. Ser. No. 955,504 filed Oct. 27, 1978, now U.S. Pat. No. 4,225,337, which is a continuation-in-part of U.S. Ser. No. 937,552, filed Sept. 1, 1978, now abandoned, which is a continuation-in-part of U.S. Ser. No. 840,168 filed Oct. 6, 1977, now abandoned.

BACKGROUND

This invention relates to novel N-(heterocyclicaminocarbonyl)arylsulfonamides wherein the aryl group thereof is substituted by an amino, isocyanato, carbamate, amido, thiocarbamate or ureido group. The compounds of this invention are useful as agricultural chemicals, such as plant growth regulants and herbicides.

Netherlands Pat. No. 121,788, published Sept. 15, 1966, discloses the preparation of compounds of the following formula and their use as general or selective herbicides:

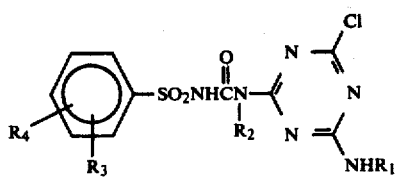

wherein $R_1$ and $R_2$ may independently be alkyl of 1–4 carbon atoms; and $R_3$ and $R_4$ may independently be hydrogen, chlorine or alkyl of 1–4 carbon atoms.

U.S. Pat. No. 3,637,366 discloses compounds having the formula:

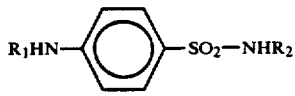

wherein $R_1$ is hydrogen or lower saturated aliphatic acyl; and $R_2$ is hydrogen, 2-pyrimidinyl, pyridyl, amidino, acetyl or carbamoyl.

The disclosed compounds are said to provide control of crabgrass, cress, endive, clover and *Poa annua*.

French Pat. No. 1,468,747 discloses the following para-substituted phenylsulfonamides as being useful as antidiabetic agents:

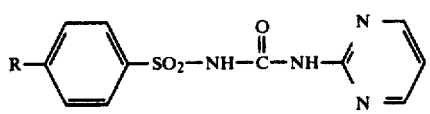

wherein R = halogen, $CF_3$ or alkyl.

Compounds of the following formula, and their use as antidiabetic agents, are reported in *J. Drug Res.* 6. 123 (1974):

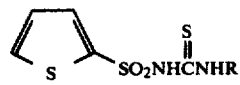

wherein R is pyridyl.

Logemann et al., Chem. Ab., 53, 18052 g (1959), disclose a number of sulfonamides, including uracil derivatives and those having the formula:

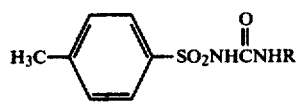

wherein R is butyl, phenyl or

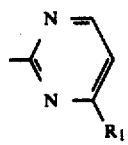

and $R_1$ is hydrogen or methyl. When tested for hypoglycemic effect in rats (oral doses of 25 mg/100 g), the compounds in which R is butyl and phenyl were most potent. The others were of low potency or inactive.

Argentine Pat. No. 174,510 (attached hereto) teaches compounds of the general formula:

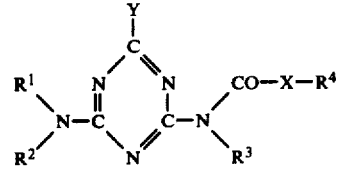

In this formula $R^1$, $R^2$ and $R_3$ are equal or different and represent hydrogen or alkyl or alkenyl groups which can also be substituted for example by —OH, —Cl, —SH, —$NO_2$ or —$NH_2$ groups. The radicals $R^1$ and $R^2$ can also be closed in the form of a five- or six-membered ring. $R^4$ represents hydrogen or an alkyl or aryl radical which can also be substituted. Between the group X and the radical $R^4$ there can also be an $SO_2$ group. X represents a bridge of oxygen, nitrogen or sulfur, which connects the CO group with a radical $R^4$. Y is an atom of chlorine or the radical —$CH_3$, —$CH_2Cl$, —$CHCl_2$ or —$CCl_3$.

Wojciechowski, J. Acta. Polon. 19, p. 121–5 (1962) [Chem. Ab., 59 1633 e] describes the synthesis of N-[(2,6-dimethoxypyrimidin-4-yl)aminocarbonyl]-4-methylbenzenesulfonamide:

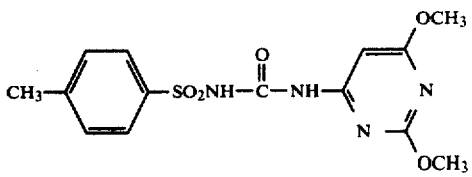

Based upon similarity to a known compound, the author predicted hypoglycemic activity for the foregoing compound.

Substituted pyrimidinyl sulfonylureas of the following formula, which are also para-substituted on the phenyl ring, are disclosed in Farmco Ed. Sci., 12, 586 (1957) [Chem. Ab., 53, 18052 g (1959)]:

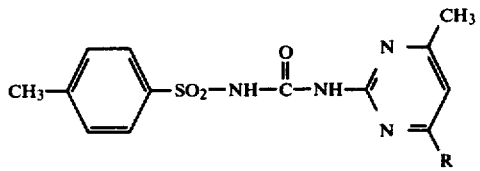

where R=H or CH$_3$.

The presence of undesired vegetation causes substantial damage to useful crops, especially agricultural products that satisfy man's basic food and fiber needs, such as cotton, rice, corn, wheat, and the like. The current population explosion and concomitant world food and fiber shortage demand improvements in producing these crops. Preventing or minimizing loss of a portion of such valuable crops by killing, or inhibiting the growth of undesired vegetation is one way of improving this efficiency.

A wide variety of materials useful for killing or inhibiting (controlling) the growth of undesired vegetation are available; such materials are commonly referred to as herbicides. However, the need still exists for effective herbicides that destroy or control weeds while not significantly damaging useful crops. Some weeds (nutsedge is a particular example) are very difficult to control; many of the herbicides that are used to control nutsedge are so nonselective that they cause damage to the crops themselves.

SUMMARY OF THE INVENTION

This invention relates to compounds of Formula I and their agriculturally suitable salts, suitable agricultural compositions containing them, and method of using them as pre-emergence and/or post-emergence herbicides:

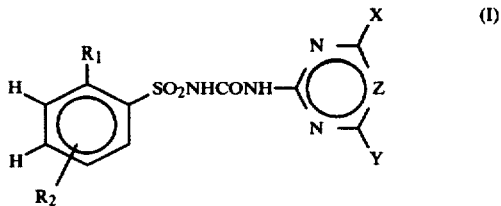

wherein

R$_1$ is H, Cl, Br, F, alkyl of 1–4 carbon atoms, OCH$_3$, NO$_2$ or R$_{11}$S(O)$_m$;

R$_2$ is —NCO, —NHCOOR$_3$, —NHCOSR$_3$, —NHCOR$_3$, —NHCONR$_4$R$_5$ or —NR$_6$R$_7$;

R$_3$ is alkyl of 1–4 carbon atoms;

R$_4$ is H or CH$_3$;

R$_5$ is H, alkyl of 1–4 carbon atoms or methoxy;

R$_6$ is H or alkyl of 1–3 carbon atoms;

R$_7$ is H or alkyl of 1–3 carbon atoms; or

R$_6$ and R$_7$ taken together are —(CH$_2$)$_n$— or —CH$_2$CH$_2$OCH$_2$CH$_2$—;

n is 4 or 5;

R$_{11}$ is alkyl of 1–3 carbon atoms;

m is 0 or 2;

X is methyl, methoxy or ethoxy;

Y is methyl or methoxy; and

Z is CH or N;

provided that:

(a) when R$_2$ is ortho to the sulfonylureido group, then R$_1$ must be hydrogen and R$_2$ cannot —NCO;

(b) when R$_5$ is methoxy, R$_4$ is methyl;

(c) when R$_2$ is —NCO, the compound cannot be a salt; and (d) when R$_2$ is —NCO, —NHCOOR$_3$ or —NHCONR$_4$R$_5$ and Z is nitrogen, then R$_1$ must be alkyl of 2–4 carbon atoms or R$_{11}$S(O)$_m$.

Preferred for their high herbicidal activity and/or favorable ease of synthesis are those compounds of Formula I wherein:

R$_2$ is —NR$_6$R$_7$, —NCO, —NHCOOCH$_3$, —NHCOCH$_3$ or —NHCON(CH$_3$)$_2$; and R$_6$ and R$_7$ are independently hydrogen or alkyl of 1–3 carbon atoms.

Also preferred for their high herbicidal activity and/or favorable ease of synthesis are those compounds of Formula I wherein:

R$_1$ is alkyl of 2–3 carbon atoms or R$_{11}$S(O)$_m$.

More preferred for their higher herbicidal activity and/or more favorable ease of synthesis are those of the preferred compounds of Formula I wherein:

R$_2$ is —NR$_6$R$_7$ or —NCO;

R$_6$ and R$_7$ are independently hydrogen or methyl; and X is methyl or methoxy.

Most preferred for their outstanding herbicidal activity and/or most favorable ease of synthesis are those of the more preferred compounds of Formula I wherein:

R$_1$ is hydrogen, chlorine, methyl or methoxy.

Specifically preferred for the same reasons are the following compounds:

Methyl [3-[[(4-methoxy-6-methylpyrimidin-2-yl)aminocarbonyl]aminosulfonyl]phenyl]carbamate;

(1-Methylethyl) [3-[[(4-methoxy-6-methylpyrimidin-2-yl)aminocarbonyl]aminosulfonyl]phenyl]carbamate;

3-isocyanato-N-[(4-methoxy-6-methylpyrimidin-2-yl)aminocarbonyl]benzenesulfonamide;

3-(3,3-dimethylureido)-N-[(4-methoxy-6-methylpyrimidin-2-yl)aminocarbonyl]benzenesulfonamide;

2-amino-N-[(4-methoxy-6-methylpyrimidin-2-yl)aminocarbonyl]benzenesulfonamide;

2-amino-N-[(4,6-dimethylpyrimidin-2-yl)aminocarbonyl]benzenesulfonamide;

5-amino-N-[(4,6-dimethylpyrimidin-2-yl)aminocarbonyl]-2-methylbenzenesulfonamide;

5-amino-N-[(4,6-dimethoxypyrimidin-2-yl)aminocarbonyl]-2-methylbenzenesulfonamide;

5-amino-N-[(4-methoxy-6-methylpyrimidin-2-yl)aminocarbonyl]-2-methylbenzenesulfonamide;

5-amino-N-[(4-methoxy-6-methyl-1,3,5-triazin-2-yl)aminocarbonyl]-2-methylbenzenesulfonamide;

5-amino-N-[(4,6-dimethoxy-1,3,5-triazin-2-yl)aminocarbonyl]-2-methylbenzenesulfonamide;

2-Methyl-5-[(methylamino)carbonylamino]-N-[(4,6-dimethoxypyrimidin-2-yl)aminocarbonyl]benzenesulfonamide;

2-Methyl-5-[(methylamino)carbonylamino]-N-[(4-methoxy-6-methylpyrimidin-2-yl)aminocarbonyl]benzenesulfonamide;

2-Amino-N-[(4,6-dimethoxypyrimidin-2-yl)aminocarbonyl]benzenesulfonamide;

2-Amino-N-[(4-methoxy-6-methyl-1,3,5-triazin-2-yl)aminocarbonyl]benzenesulfonamide;

N-[2-[[(4,6-Dimethoxypyrimidin-2-yl)aminocarbonyl]aminosulfonyl]phenyl]acetamide;

N-2[-[[(4-Methoxy-6-methylpyrimidin-2-yl)aminocarbonyl]aminosulfonyl]phenyl]acetamide; and N-[2-[[(4,6-Dimethylpyrimidin-2-yl)aminocarbonyl]aminosulfonyl]phenyl]acetamide.

Synthesis

As shown in Equation 1, the compounds of Formula I wherein $R_2$ is isocyanato can be prepared by combining an appropriate 2-aminopyrimidine or 2-amino-1,3,5-triazine of Formula III with an appropriately substituted m-isocyanatobenzenesulfonamide of Formula II; $R_1$, X, Y and Z being as previously defined.

Equation 1

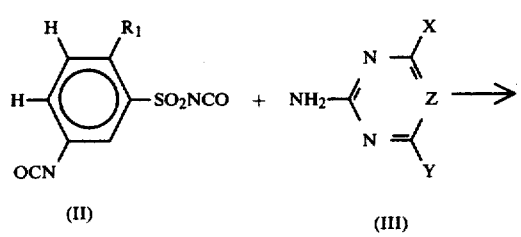

(I-A)

The reaction is best carried out in inert aprotic organic solvents such as methylene chloride, tetrahydrofuran or acetonitrile, at ambient pressure and temperature. The aminoheterocycle (III) is added slowly to a solution of the m-isocyanatobenzenesulfonyl isocyanate with stirring. Such slow addition favors reaction of the amine with the highly active sulfonyl isocyanate moiety of compound (II) rather than the aryl isocyanate moiety thereof.

The reaction is generally exothermic. In some cases, the desired product is insoluble in the warm reaction medium and crystallizes from it in pure form. Products soluble in the reaction medium are isolated by evaporation of the solvent, trituration of the solid residue with solvents such as 1-chlorobutane, ethyl ether or pentane, and filtration.

The intermediate m-isocyanatobenzenesulfonyl isocyanates of Formula II can be prepared from the corresponding m-amino-N-(butylcarbamoyl)benzenesulfonamides by reaction with phosgene according to H. Ulrich, B. Tucker and A. A. R. Sayigh, J. Org. Chem. 31, 2658–2661 (1966).

The isocyanato substituent in compound (I-A) can be converted readily to the carbamates (I-B), thiolcarbamates (I-C), or urea derivatives (I-D) of this invention by reaction thereof respectively with the appropriate alcohol (Equation 2), thiol (Equation 3) or amine (Equation 4).

Equation 2.

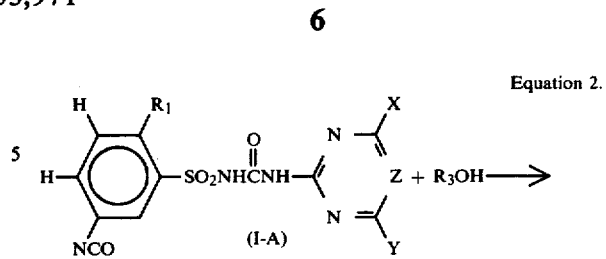

Equation 3.

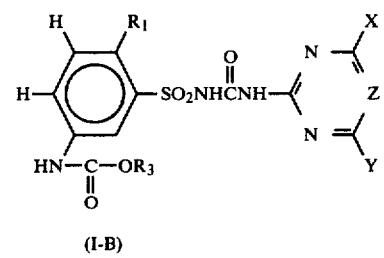

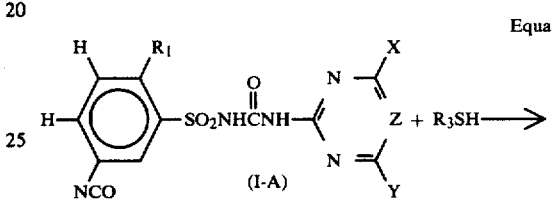

Equation 4.

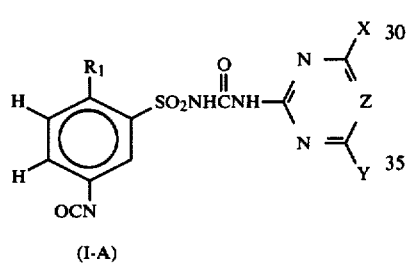

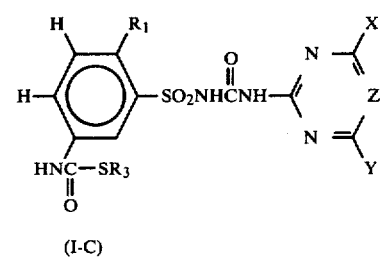

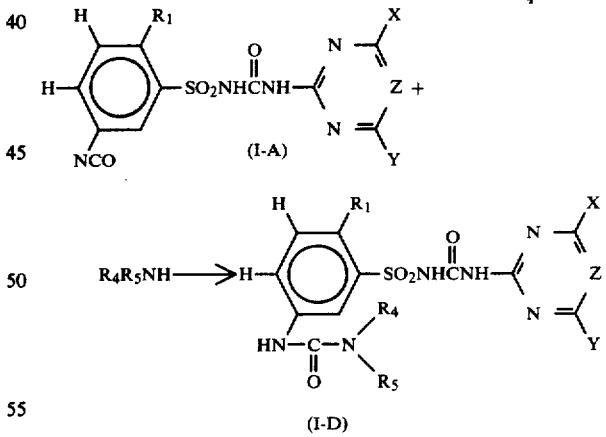

The reactions of Equation 2, 3 or 4 can be carried out in situ with isocyanato compound (I-A), or isocyanato compound (I-A) can first be isolated and added to the alcohol, thiol, or amine neat or in a non-reactive solvent. In any event, the reactions of Equations 2, 3 and 4 proceed readily and are mildly exothermic; however, in some cases, the addition of a catalyst such as dibutyl tin dilaurate or 1,4-diazabicyclooctane may be used.

As shown in Equation 5, the compounds of Formula I wherein $R_2$ is amino can be prepared by the catalytic hydrogenation of appropriately substituted N- rimidinylaminocarbonyl)nitrobenzenesulfonamide
N-(triazinylaminocarbonyl)nitrobenzenesulfonamide
hich are disclosed in my previously filed applications
:. No. 824,805, filed Aug. 15, 1977 and Ser. No.
),389 filed Oct. 10, 1977, the contents of which are
orporated herein by reference):

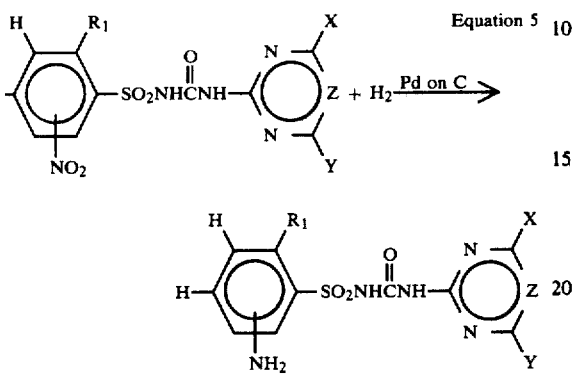

Equation 5 e reaction of Equation 5 is best carried out in polar vents such as acetic acid or ethanol in the presence of o 10% palladium on carbon at ambient temperature der hydrogen pressure of 1 to 5 atmospheres. The ino compounds thus prepared can be acylated by yl halides of the appropriate carboxylic acids according to Equation 6.

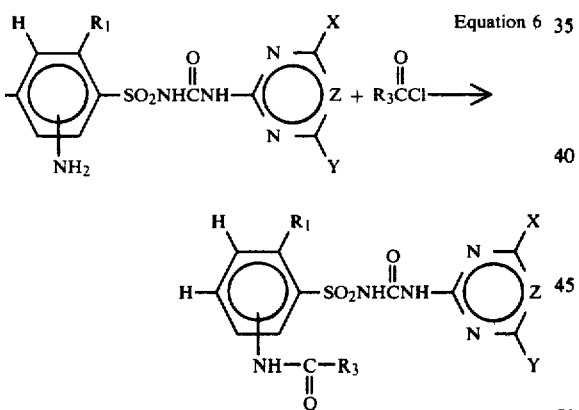

Equation 6 iese acylations are best carried out in a polar aprotic lvent such as methylene chloride or acetonitrile in the esence of an acid acceptor such as pyridine, collidine triethylamine. Frequently the best results are obned by combining the acylating agent and acid acceptr in the anhydrous solvent prior to the addition of the nzenesulfonamide.

In other cases, acylation of the aminobenzenesulfonaides as described in Equation 7 is best carried out by ing the appropriate anhydride as a solvent for the action or adding a two-fold excess of the appropriate hydride to a warm concentrated solution of a suitable ninobenzenesulfonamide in a solvent such as chlororm or methylene chloride and refluxing from one to hours.

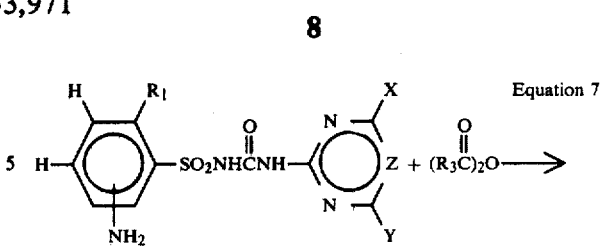

Equation 7

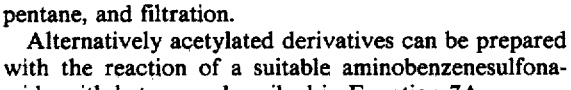

In some cases, the desired product is insoluble in the warm reaction medium and crystallizes from it in pure form. Products soluble in the reaction medium are isolated by evaporation of the solvent, excess anhydride and the corresponding acid, trituration of the residue with solvent such as 1-chlorobutane, ethyl ether or pentane, and filtration.

Alternatively acetylated derivatives can be prepared with the reaction of a suitable aminobenzenesulfonamide with ketene as described in Equation 7A.

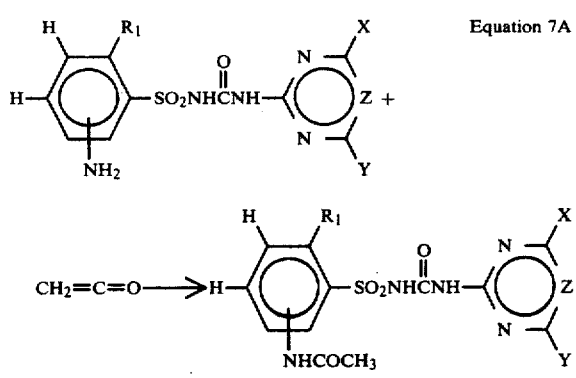

Equation 7A

The reaction of Equation 7A is carried out by suspending the aminobenzenesulfonamide in a solvent such as methylenechloride, chloroform or tetrahydrofuran, treating the suspension with an excess of ketene gas at ambient temperature and allowing the mixture to stand for one to three hours. The product is isolated by removing the solvent by evaporation and triturating the residue with water to hydrolyze the by-products and cause the product to solidify.

Ureido-substituted compounds can be prepared by reaction of the appropriate amine with a dialkylcarbamoyl chloride in the presence of an acid acceptor, such as pyridine, (Equation 8) or an alkyl isocyanate (Equation 9) neat or in aprotic solvent such as toluene, chloroform, or methylene chloride.

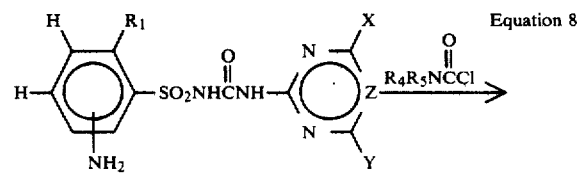

Equation 8

-continued

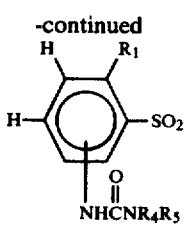
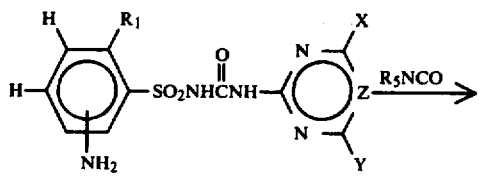 Equation 9
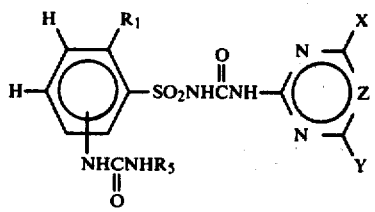

Generally, N-alkyl- or N,N-dialkylaminobenzenesulfonamides can be prepared as shown in Equation 10 by reacting the appropriate aminobenzenesulfonamide in acetonitrile with an aqueous or acetonitrile solution of a suitable aldehyde and sodium cyanoborohydride at room temperature and ambient pressure in a modification of the procedure taught by R. F. Borch and A. I. Hassid, *J. Org. Chem.*, 37, 1673 (1972).

Equation 10

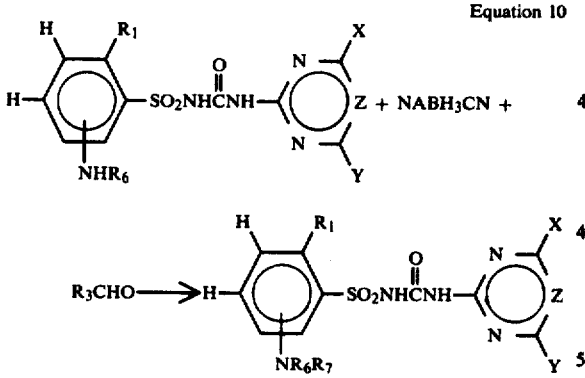

Alkylation of secondary aminobenzenesulfonamides can be effected using a 3-10 fold excess of the appropriate aldehyde in the presence of sodium cyanoborohydride. After the addition of the aldehyde, glacial acetic acid is added intermittently to adjust the pH to neutrality. Following additional stirring and dilution with water, the pH is again adjusted to neutrality and the desired products are isolated by extraction with a suitable solvent, such as chloroform, methylene chloride or ether, followed by evaporation of solvent and trituration of the residue with solvents such as 1-chlorobutane, ethyl ether or pentane, and filtration.

Compounds wherein a dialkylamino, morpholino or pyrrolidino group is meta to the sulfonyl can be prepared by the reaction of an appropriately substituted benzenesufonylisocyanate with the appropriate 2-aminopyrimdine or 2-amino-1,3,5-triazine according to Equation 11.

Equation 11

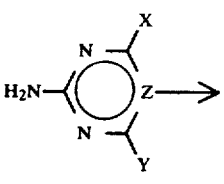
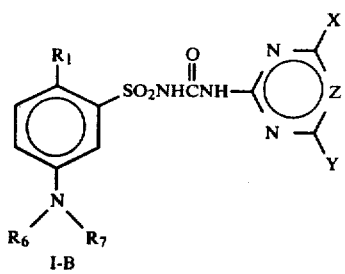

The reaction is best carried out in inert aprotic organic solvents such as methylene chloride, tetrahydrofuran or acetonitrile, at ambient temperature. The aminoheterocycle (III-B) is suspended in the solvent and the sulfonyl isocyanate (II-B) is added to the suspension. A mildly exothermic reaction generally occurs which results in a warm reaction mixture from which many of the desired compounds (I-B) crystallize in pure form.

As shown in Equation 12, the carbamates I-B and I-C, as well as those compounds of Formula I wherein the carbamate or thiocarbamate group is located ortho to the sulfonyl group, can be prepared by reacting the appropriate amino-precursor therefor with an appropriate chloroformate ester under the conditions described for the reactions of Equations 8 and 9.

Equation 12

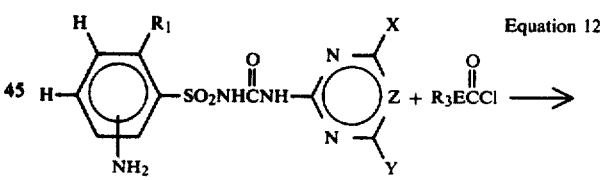

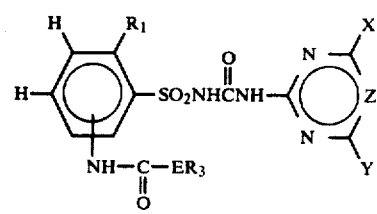

wherein E is O or S.

The sulfonated intermediates required for the reaction of Equation 11 can be prepared by way of chlorosulfonation, using methods reported in the literature [cf. Holleman, Rec. Trav. Chim. 24, 31 (1905)]. When $R_1$ is nitro, displacement of chlorine by reacting an appropriate secondary amine with 5-chloro-2-nitrobenzenesulfonamide in a suitable solvent such as ethanol will afford the required starting material for the preparation of II-B.

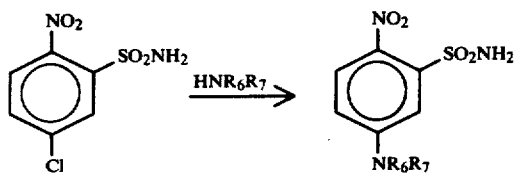

The preparation of 5-chloro-2-nitrobenzenesulfonamide is described by J. G. Topliss et al., *J. Med. Chem.* 6, 122 (1963).

Other sulfonyl chlorides, useful as intermediates for the preparation of compounds of this invention, are prepared by diazotization of the appropriate aniline with sodium nitrite in HCl, followed by the reaction of the diazonium salt with sulfur dioxide and cuprous chloride in acetic acid according to the teaching of H. L. Yale and F. Sowinski, *J. Org. Chem.* 25, 1824 (1960). The preparation of sulfonamides from sulfonyl chlorides and ammonium hydroxide is widely reported in the literature, e.g., Crossley et al., *J. Am. Chem. Soc.* 60, 2223 (1938).

The intermediate sulfonyl isocyanates of Formulae II and IIb can be prepared by reacting corresponding sulfonamides with phosgene in the presence of n-butyl isocyanate at reflux in a solvent such as chlorobenzene, according to the procedure of H. Ulrich and A. A. Y. Sayigh, "Newer Methods of Preparative Organic Chemistry", Vol. VI p. 223-241, Academic Press, New York and London, W. Foerst Ed. In cases where formation of the desired sulfonyl isocyanate is difficult by the above procedure the sulfonylurea formed by reaction of butyl isocyanate with the appropriate sulfonamide is treated with phosgene according to the above reference.

When $R_1$ is $R_{11}S(O)_m$ sulfonated intermediates can be prepared via chlorosulfonation [F. Holleman, above] of the appropriate alkyl nitrobenzene sulfide. The sulfonyl chloride thus obtained is converted to the sulfonamide and sulfonyl isocyanate as previously discussed. Oxidation of the o-alkylthiobenzenesulfonamide intermediates to sulfones ($R_1=R_{11}SO_2$) can be carried out in acetic acid with 30% hydrogen peroxide according to methods cited by C. M. Suter in "Organic Chemistry of Sulfur", John Wiley and Sons, Inc., New York, N.Y. 1944.

As shown in Equation 13 below, the acid addition salts of 2- or 5-aminocarbonylbenzenesulfonamides can be prepared by heating at 40°-50° a suspension of the appropriate aminobenzenesulfonamide in a solvent such as ethanol containing an equivalent amount of an acid such as HCl, HBr, $H_2SO_4$, p-toluenesulfonic acid or trichloroacetic acid. In the case of volatile mineral acids such as HCl or organic acids such as trichloroacetic acid an excess may be employed. Removal of solvent in vacuo yields the desired ammonium salt.

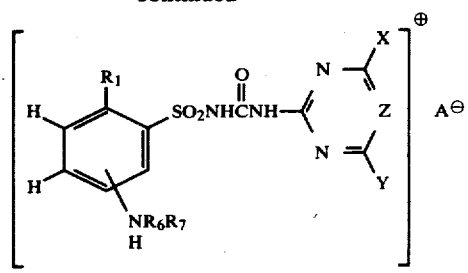

The alkali metal salts of substituted benzenesulfonamides can be prepared as shown in Equation 14. The alkali metal salts can be obtained by addition of one equivalent of the appropriate base such as metal alkoxide, hydroxide, or carbonate in a solvent such as methanol or ethanol to a suspension of the appropriate benzenesulfonamide, in the same solvent, followed by heating at 40°-50° and removal of solvent under reduced pressure. Residues are usually glasses which may be triturated with solvents such as ethylacetate, ethylether or hexane to give the desired solid alkali metal salts.

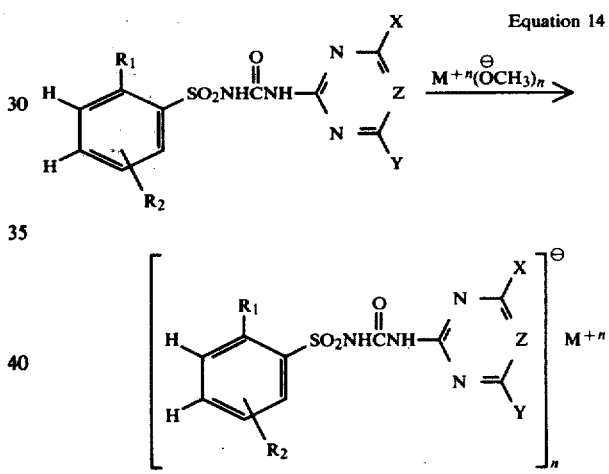

The ammonium salts of substituted benzenesulfonamides can be prepared as described in Equation 15. Generally one equivalent of an appropriate amine such as ammonia, dimethylamine, diethanolamine or triethanolamine is added neat or in a solvent such as methylene chloride or methanol to a suspension of the appropriate benzenesulfonamide in the same solvent. The solvent is removed under reduced pressure to yield as product, the desired ammonium salt.

In the following equation, equation 15, $R_8$, $R_9$, and $R_{10}$ are independently selected from $C_1$-$C_{15}$ alkyl, $CH_2CH_2OH$ and phenyl.

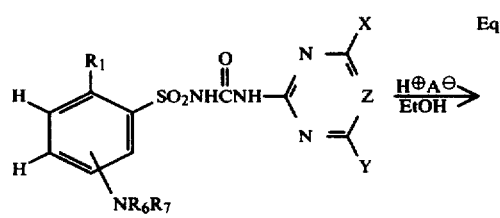

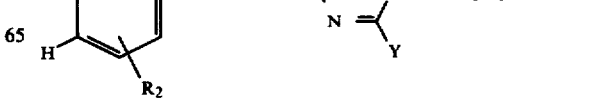

-continued

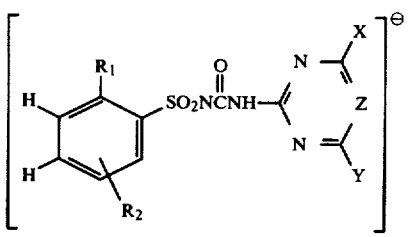

The synthesis of aminoheterocyclic derivatives has been reviewed in "The Chemistry of Heterocyclic Compounds", a series published by Interscience Publ., New York and London. 2-Aminopyrimidines are described by D. J. Brown in "The Pyrimidines", Vol. XVI of the above series published in 1962. 2-Amino-1,3,5-triazines are synthesized according to methods cited by E. M. Smolin and L. Rapaport in "s-Triazines and Derivatives", Vol. XIII of this series, published 1959.

The preparation of compounds of this invention is further illustrated by the following specific examples wherein temperatures are in degrees C.

EXAMPLE 1

3-Isocyanato-N-[(4-methoxy-6-methyl-1,3,5-triazin-2-yl)aminocarbonyl]benzenesulfonamide To 21 g of m-isocyantobenzenesulfonyl isocyanate in 250 ml of anhydrous acetonitrile was added in small portions at ambient temperature, 14 g of 2-amino-4-methoxy-6-methyl-1,3,5-triazine, and the mixture was stirred at ambient temperature for sixteen hours. The white precipitate thus obtained was removed by filtration and dried in vacuo. The resultant product, m.p. 260° dec, which is 3-isocyanato-N-[(4-methoxy-6-methyl-1,3,5-triazin-2-yl)aminocarbonyl]benzenesulfonamide, showed an infrared absorption peak at 2210 cm$^{-1}$, consistent for the desired compound containing one isocyanate function.

By using the procedure of Example 1 with an equivalent amount of an appropriate 2-aminopyrimidine or 2-amino-1,3,5-triazine and an appropriately substituted m-isocyanatobenzenesulfonyl isocyanate, the compounds of Table I can be prepared.

TABLE I

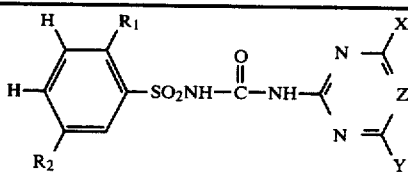

| $R_1$ | $R_2$ | X | Y | Z |
|---|---|---|---|---|
| H | NCO | $CH_3$ | $CH_3$ | CH |
| H | NCO | $CH_3$ | $OCH_3$ | CH |
| H | NCO | $OCH_3$ | $OCH_3$ | CH |
| H | NCO | $CH_3$ | $CH_3$ | N |
| H | NCO | $OCH_3$ | $OCH_3$ | N |
| Cl | NCO | $OCH_3$ | $OCH_3$ | CH |
| Cl | NCO | $OCH_3$ | $CH_3$ | CH |
| Cl | NCO | $OCH_3$ | $OCH_3$ | N |
| Cl | NCO | $OCH_3$ | $CH_3$ | N |
| Br | NCO | $OCH_3$ | $CH_3$ | CH |
| Br | NCO | $OCH_3$ | $OCH_3$ | CH |
| Br | NCO | $OCH_3$ | $OCH_3$ | N |
| $CH_3$ | NCO | $OCH_3$ | $CH_3$ | CH |
| $CH_3$ | NCO | $OCH_3$ | $OCH_3$ | CH |
| $CH_3$ | NCO | $OCH_3$ | $OCH_3$ | N |
| F | NCO | $OCH_3$ | $CH_3$ | CH |

TABLE I-continued

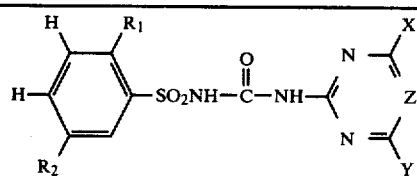

| $R_1$ | $R_2$ | X | Y | Z |
|---|---|---|---|---|
| F | NCO | $OCH_3$ | $OCH_3$ | CH |
| F | NCO | $OCH_3$ | $OCH_3$ | N |
| $OCH_3$ | NCO | $OCH_3$ | $CH_3$ | CH |
| $OCH_3$ | NCO | $OCH_3$ | $OCH_3$ | CH |
| $OCH_3$ | NCO | $OCH_3$ | $OCH_3$ | N |
| $NO_2$ | NCO | $OCH_3$ | $CH_3$ | N |
| $NO_2$ | NCO | $OCH_3$ | $OCH_3$ | CH |
| $NO_2$ | NCO | $OCH_3$ | $CH_3$ | CH |
| $CH_2CH_3$ | NCO | $CH_3$ | $CH_3$ | CH |
| $CH_2CH_3$ | NCO | $CH_3$ | $OCH_3$ | CH |
| $CH_2CH_2CH_3$ | NCO | $CH_3$ | $OCH_3$ | CH |
| $CH(CH_3)_2$ | NCO | $CH_3$ | $OCH_3$ | CH |
| $SCH_3$ | NCO | $CH_3$ | $OCH_3$ | CH |
| $SCH_2CH_2$ | NCO | $CH_3$ | $OCH_3$ | CH |
| $SCH(CH_3)_2$ | NCO | $CH_3$ | $OCH_3$ | CH |
| $SO_2CH_2CH_2CH_3$ | NCO | $CH_3$ | $OCH_3$ | CH |
| $SO_2CH(CH_3)_2$ | NCO | $CH_3$ | $OCH_3$ | CH |
| $SO_2CH_2CH_3$ | NCO | $CH_3$ | $OCH_3$ | CH |
| $SO_2CH_3$ | NCO | $CH_3$ | $OCH_3$ | CH |
| $SO_2CH_3$ | NCO | $OCH_3$ | $OCH_3$ | N |
| $SO_2CH_3$ | NCO | $OCH_3$ | $CH_3$ | N |
| $SO_2CH_2CH_3$ | NCO | $OCH_3$ | $CH_3$ | N |
| $SO_2CH_2CH_2CH_3$ | NCO | $OCH_3$ | $CH_3$ | N |

EXAMPLE 2

Methyl [3-[[(4-methoxy-6-methylpyrimidin-2-yl)aminocarbonyl]aminosulfonyl]phenyl]carbamate To an anhydrous solution containing 2.1 g of m-isocyanatobenzenesulfonyl isocyanate and 30 ml of acetonitrile was added in small portions at ambient temperature, 1.4 g of 2-amino-4-methoxy-6-methylpyrimidine with stirring. The mixture was stirred for sixteen hours at ambient temperature, followed by the addition of 1 g of anhydrous methanol. Evaporation of the solvent yielded a gelatinous product which solidified when triturated with ethyl ether. The desired product thus obtained decomposed at above 120°.

EXAMPLE 3

(1-Methylethyl) [3-[[(4-methoxy-6-methylpyrimidin-2-yl)aminocarbonyl]aminosulfonyl]phenyl]carbamate To an anhydrous solution of 2.3 g of m-isocyanatobenzenesulfonyl isocyanate in 50 ml of methylene chloride was added in small portions 1.4 g of 2-amino-4-methoxy-6-methylpyrimidine. Efficient stirring was maintained during the addition and for three additional hours. The intermediate thus obtained, 3-isocyanto-N-[(4-methoxy-6-methylpyrimidin-2-yl)aminocarbonyl]benzenesulfonamide, was reacted further by adding one gram of 2 -propanol and stirring the resultant mixture for an additional sixteen hours. Filtration of the reaction mixture and evaporation of the filtrate yielded the desired product melting at 173°–180°.

By using the procedure of Example 2 or 3 with equivalent amounts of an appropriate 2-aminopyrimidine or 2-amino-1,3,5-triazine, an appropriate m-isocyanatobennesulfonyl isocyanate, and an appropriate alcohol or iol, the compounds of Table II can be prepared.

TABLE II

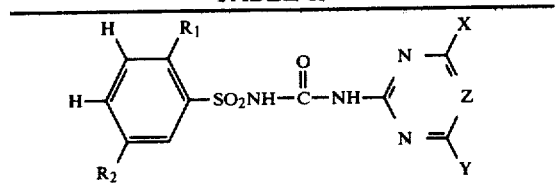

| R1 | R2 | X | Y | Z |
|---|---|---|---|---|
|  | NHCO2CH3 | OCH3 | OCH3 | CH |
|  | NHCO2CH3 | OCH3 | CH3 | N |
|  | NHCO2CH3 | OCH3 | OCH3 | N |
|  | NHCO2CH3 | OCH3 | CH3 | N |
|  | NHCO2CH3 | OCH3 | OCH3 | CH |
|  | NHCO2CH3 | OCH3 | CH3 | CH |
|  | NHCO2CH3 | OCH3 | OCH3 | N |
| H3 | NHCO2CH3 | OCH3 | OCH3 | CH |
| H3 | NHCO2CH3 | OC2H5 | CH3 | CH |
| H3 | NHCO2CH3 | OCH3 | OCH3 | N |
|  | NHCO2CH3 | OCH3 | OCH3 | CH |
| r | NHCO2CH3 | OCH3 | CH3 | CH |
| r | NHCO2CH3 | OC2H5 | OCH3 | N |
|  | NHCO2CH3 | OC2H5 | OCH3 | CH |
|  | NHCO2CH3 | OCH3 | CH3 | CH |
|  | NHCO2CH3 | OCH3 | CH3 | N |
| CH3 | NHCO2CH3 | OCH3 | OCH3 | CH |
| CH3 | NHCO2CH3 | OC2H5 | CH3 | CH |
| CH3 | NHCO2CH3 | OCH3 | OCH3 | N |
|  | NHCO2C2H5 | OCH3 | OCH3 | CH |
|  | NHCO2C2H5 | OCH3 | CH3 | N |
| O2 | NHCO2CH3 | OCH3 | CH3 | N |
| IO2 | NHCO2CH3 | OCH3 | OCH3 | CH |
| IO2 | NHCO2CH3 | OCH3 | CH3 | CH |
| I | NHCO2C2H5 | OCH3 | OCH3 | N |
| :I | NHCO2C2H5 | OCH3 | CH3 | CH |
| :H3 | NHCO2C2H5 | OCH3 | CH3 | CH |
| r | NHCO2C2H5 | OCH3 | CH3 | CH |
|  | NHCO2C2H5 | OCH3 | OCH3 | CH |
| )CH3 | NHCO2C2H5 | OCH3 | OCH3 | CH |
| I | O<br>‖<br>NHCSCH3 | OCH3 | OCH3 | CH |
| :H3 | O<br>‖<br>NHCSCH3 | OCH3 | CH3 | CH |
| :l | O<br>‖<br>NHCSCH3 | OCH3 | OCH3 | CH |
| = | O<br>‖<br>NHCSCH3 | OCH3 | OCH3 | N |
| Br | O<br>‖<br>NHCSCH3 | OCH3 | CH3 | N |
| OCH3 | O<br>‖<br>NHCSCH3 | OCH3 | OCH3 | N |
| H | O<br>‖<br>NHCSC2H5 | OCH3 | OCH3 | N |
| CH3 | O<br>‖<br>NHCSC2H5 | OCH3 | OCH3 | CH |
| Cl | O<br>‖<br>NHCSC2H5 | OCH3 | CH3 | CH |
| OCH3 | O<br>‖<br>NHCSC2H5 | OCH3 | OCH3 | N |

TABLE II-continued

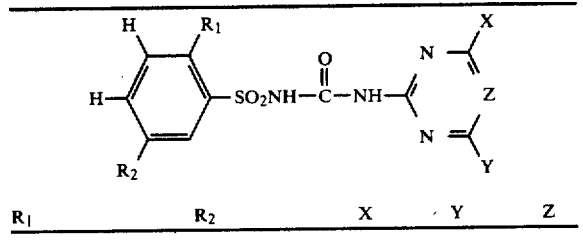

| R1 | R2 | X | Y | Z |
|---|---|---|---|---|
| H | O<br>‖<br>NHC—S—i-C3H7 | OCH3 | OCH3 | N |
| H | O<br>‖<br>NHCS—N-C3H7 | OC2H5 | OCH3 | CH |
| Cl | NHCO2i-C3H7 | OCH3 | OCH3 | CH |
| F | NHCO2i-C3H7 | OCH3 | OCH3 | N |
| CH3 | NHCO2i-C3H7 | OCH3 | CH3 | N |
| OCH3 | NHCO2i-C3H7 | CH3 | CH3 | CH |
| H | NHCO2n-C3H7 | OC2H5 | CH3 | CH |
| Cl | NHCO2n-C3H7 | OCH3 | OCH3 | CH |
| F | NHCO2n-C3H7 | OCH3 | OCH3 | CH |
| Br | NHCO2n-C3H7 | OCH3 | CH3 | CH |
| OCH3 | NHCO2n-C3H7 | OCH3 | OCH3 | CH |
| CH2CH3 | NHCO2CH3 | CH3 | OCH3 | CH |
| CH2CH2CH3 | NHCO2CH3 | CH3 | OCH3 | CH |
| CH(CH3)2 | NHCO2CH3 | CH3 | OCH3 | CH |
| CH2CH3 | NHCO2CH3 | CH3 | OCH3 | N |
| CH2CH2CH3 | NHCO2CH3 | CH3 | OCH3 | N |
| CH(CH3)2 | NHCO2CH3 | CH3 | OCH3 | N |
| CH(CH3)2 | NHCO2CH3 | OCH3 | OCH3 | CH |
| SCH3 | NHCO2CH3 | OCH3 | OCH3 | CH |
| SCH2CH3 | NHCO2CH3 | OCH3 | OCH3 | CH |
| SCH2CH2CH3 | NHCO2CH3 | OCH3 | OCH3 | CH |
| SCH(CH3)2 | NHCO2CH3 | OCH3 | OCH3 | CH |
| SCH3 | NHCO2CH3 | CH3 | OCH3 | N |
| SCH2CH3 | NHCO2CH3 | CH3 | OCH3 | N |
| SCH2CH2CH3 | NHCO2CH3 | CH3 | OCH3 | N |
| SCH(CH3)2 | NHCO2CH3 | CH3 | OCH3 | N |
| SO2CH3 | NHCO2CH3 | OCH3 | OCH3 | CH |
| SO2CH2CH3 | NHCO2CH3 | OCH3 | OCH3 | CH |
| SO2CH2CH2CH3 | NHCO2CH3 | OCH3 | OCH3 | CH |
| SO2CH3 | NHCO2CH3 | CH3 | OCH3 | N |
| SO2CH2CH3 | NHCO2CH3 | CH3 | OCH3 | N |
| SO2CH2CH2CH3 | NHCO2CH3 | CH3 | OCH3 | N |
| SO2CH(CH3)2 | NHCO2CH3 | CH3 | OCH3 | N |

EXAMPLE 4

3-(3,3-Dimethylureido)-N-[(4-methoxy-6-methylpyrimidin-2-yl)aminocarbonyl]benzenesulfonamide A solution of 3-isocyanato-N-[(4-methoxy-6-methylpyrimidin-4-yl)aminocarbonyl]benzenesulfonamide was prepared as in Example 3 and to this was added 0.5 ml of liquified anhydrous dimethyl amine with stirring. The resultant mixture was stirred for an additional sixteen hours and evaporated in vacuo to dryness. Trituration of the residue with ethyl ether and filtration yielded the desired solid product. The product was dissolved in water by the addition of 50% sodium hydroxide to pH 13, filtered, and the filtrate adjusted to pH 3 to cause precipitation of the desired product, m.p. 147°-157°.

EXAMPLE 5

3-(3-tert-Butylureido)-N-[(4-methoxy-6-methylpyrimidin-2-yl)aminocarbonyl]benzenesulfonamide To a solution of 3-isocyanato-N-[(4-methoxy-6-methylpyrimidin-2-yl)aminocarbonyl]benzenesulfonamide prepared as in Example 3 was added 0.8 g of tert-butylamine at ambient temperature with stirring. After sixteen hours, filtration of the reaction mixture and evaporation of the filtrate yielded the desired product which after trituration with ethyl ether and isolation by filtration melted at 137°–145°.

By using the procedure of Example 4 or 5 with equivalent amounts of an appropriate 2-aminopyrimidine or 2-amino-1,3,5-triazine; an appropriate m-isocyanatobenzenesulfonyl isocyanate, and an appropriate alkyl amine, the compounds of Table III can be prepared.

TABLE III $$\text{R}_1\text{-C}_6\text{H}_3(\text{R}_2)\text{-SO}_2\text{NH-C(O)-NH-C(=N-CX(Y))(N=CZ)}$$

| $R_1$ | $R_2$ | X | Y | Z | m.p. |
|---|---|---|---|---|---|
| H | NHC(O)NHCH$_3$ | OCH$_3$ | OCH$_3$ | CH | |
| Cl | NHC(O)NHCH$_3$ | OCH$_3$ | OCH$_3$ | CH | |
| CH$_3$ | NHC(O)NHCH$_3$ | OCH$_3$ | CH$_3$ | CH | 155–157° C. |
| F | NHC(O)NHCH$_3$ | OCH$_3$ | OCH$_3$ | N | |
| OCH$_3$ | NHC(O)NHCH$_3$ | OCH$_3$ | OCH$_3$ | N | |
| H | NHC(O)N(CH$_3$)$_2$ | OCH$_3$ | CH$_3$ | N | |
| Cl | NHC(O)N(CH$_3$)$_2$ | OCH$_3$ | OCH$_3$ | N | |
| Cl | NHC(O)N(CH$_3$)$_2$ | OCH$_3$ | CH$_3$ | CH | |
| F | NHC(O)N(CH$_3$)$_2$ | OCH$_3$ | OCH$_3$ | CH | |
| CH$_3$ | NHC(O)N(CH$_3$)$_2$ | OCH$_3$ | OCH$_3$ | N | |
| OCH$_3$ | NHC(O)N(CH$_3$)$_2$ | OCH$_3$ | OCH$_3$ | N | |
| H | NHC(O)N(CH$_3$)C$_2$H$_5$ | OCH$_3$ | OCH$_3$ | N | |
| H | NHC(O)N(OCH$_3$)CH$_3$ | OCH$_3$ | OCH$_3$ | N | |
| Cl | NHC(O)N(OCH$_3$)CH$_3$ | OCH$_3$ | OCH$_3$ | CH | |
| NO$_2$ | NHC(O)N(CH$_3$)$_2$ | OCH$_3$ | CH$_3$ | CH | |
| NO$_2$ | NHC(O)N(CH$_3$)$_2$ | OCH$_3$ | OCH$_3$ | CH | |
| NO$_2$ | NHC(O)N(CH$_3$)$_2$ | OCH$_3$ | CH$_3$ | N | |

TABLE III-continued

Structure: benzene ring with R1, R2 substituents, -SO2NH-C(=O)-NH- linked to a 6-membered ring with N=X, Z, N=Y positions.

| R1 | R2 | X | Y | Z | m.p. |
|---|---|---|---|---|---|
| F | NHCN(OCH3)CH3 (with C=O) | OCH3 | OCH3 | N | |
| F | NHCN(CH3)i-C3H7 (with C=O) | OCH3 | OCH3 | N | |
| Cl | NHCN(CH3)n-C3H7 (with C=O) | OCH3 | OCH3 | N | |
| Cl | NHCN(CH3)2 (with C=O) | OCH3 | CH3 | N | |
| Cl | NHCNHtert-C4H9 (with C=O) | OCH3 | OCH3 | N | |
| H | NHCNHtert-C4H9 (with C=O) | OCH3 | OCH3 | N | |
| H | NHCN(CH3)n-C4H9 (with C=O) | OCH3 | OCH3 | N | |
| CH2CH3 | NHCON(CH3)2 | OCH3 | OCH3 | CH | |
| CH(CH3)2 | NHCON(CH3)2 | OCH3 | OCH3 | CH | |
| SO2CH3 | NHCON(CH3)2 | OCH3 | OCH3 | CH | |
| SO2CH2CH3 | NHCON(CH3)2 | OCH3 | OCH3 | CH | |
| SO2CH2CH2CH3 | NHCON(CH3)2 | OCH3 | OCH3 | CH | |
| CH2CH3 | NHCONHCH3 | CH3 | OCH3 | N | |
| CH(CH3)2 | NHCONHCH3 | CH3 | OCH3 | N | |
| SO2CH3 | NHCONHCH3 | CH3 | OCH3 | N | |
| SO2CH2CH3 | NHCONHCH3 | CH3 | OCH3 | N | |
| SO2CH2CH2CH3 | NHCONHCH3 | CH3 | OCH3 | N | |
| CH3 | NHCONHCH3 | OCH3 | OCH3 | CH | 216–218° C. |
| CH3 | NHCONHCH3 | CH3 | CH3 | CH | 188–190° C. |

EXAMPLE 6

2-Amino-N-[(4,6-dimethylpyrimidin-2-yl)aminocarbonyl]benzenesulfonamide

A suspension containing 1 g of N-[(4,6-dimethylpyrimidin-2-yl)aminocarbonyl]-2-nitrobenzenesulfonamide, 0.2 g of 5% palladium on carbon and 50 ml of ethanol was shaken in a Paar apparatus under 40 p.s.i.g. hydrogen at ambient temperature. After one hour, the reaction mixture was filtered and the solids thereby recovered, which contained catalyst and desired product, was stirred with 10% aqueous sodium hydroxide. Filtration of that mixture and acidification of the filtrate with hydrochloric acid to pH 3 caused the desired product to precipitate. After removal by filtration and drying, the desired product melted at 212°–216° and showed infrared absorption peaks at 3200 and 3300 cm$^{-1}$, consistent for the desired amino-containing compound. Mass spectrometry showed two particles of mass 198 and 123 units, equivalent to aminobenzenesulfonyl isocyanate and 2-amino-4,6-dimethylpyrimidine respectively, as expected for the desired compound.

EXAMPLE 7

2-Amino-N-[(4-methoxy-6-methylpyrimidin-2-yl)aminocarbonyl]benzenesulfonamide

A suspension containing 2 g of the sodium salt of N-[(4-methoxy-6-methylpyrimidin-2-yl)aminocarbonyl]-2-nitrobenzenesulfonamide, 25 ml of glacial acetic acid and 0.2 g of 10% palladium on carbon was shaken in a Paar apparatus at 40 p.s.i.g. hydrogen at ambient temperature. After twenty-four hours, no further pressure drop was observed. The reaction mixture was filtered and the filtrate stripped to yield a small amount of the desired product. The solids which contained most of the product and catalyst, were stirred with 20 ml of 5% aqueous sodium hydroxide, filtered and the filtrate combined with the residue from the acetic acid filtrate. After refiltering the resultant alkaline solution, it was acidified to pH 3 with dilute hydrochloric acid to precipitate the desired compound. After filtration and drying, the compound, when heated to 160°, underwent a transformation in physical appearance and subsequently melted at 210°–215°. The infrared absorption spectrum for the compound showed absorption peaks at 3300 and 3400 cm$^{-1}$, consistent for an amino substituent, and absorption bands at 1700, 1690, 1600 and 1550 cm$^{-1}$ which are consistent for the amino-carbonyl sulfonamide function. The product thus obtained was sufficiently pure for the purposes of this invention.

EXAMPLE 7a

5-Amino-N-[(4-methoxy-6-methylpyrimidin-2-yl)aminocarbonyl]-2-methylbenzenesulfonamide A suspension containing 8 g of N-[(4-methoxy-6-methylpyrimidin-2-yl)aminocarbonyl]-2-methyl-5-nitrobenzenesulfonamide, 0.5 g of 10% palladium on carbon and 150 ml of glacial acetic acid was shaken in a Paar apparatus under 40 p.s.i.g. hydrogen and ambient temperature. After ten hours, no further pressure drop was observed. The product, which was isolated as described in Example 7, melted with decomposition at 160°. It was sufficiently pure for the purposes of this invention.

By using the procedure of Example 6, 7 or 7a with equivalent amounts of an appropriate nitro-N-[(pyrimidin-2-yl)aminocarbonyl]benzenesulfonamide or nitro-N-[(1,3,5-triazin-2-yl)aminocarbonyl]benzenesulfonamide, the compounds of Table IV can be prepared.

TABLE IV

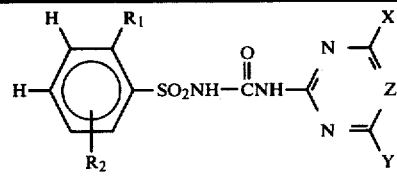

| R₁ | R₂ | X | Y | Z | m.p. |
|---|---|---|---|---|---|
| H | 2-NH₂ | CH₃ | CH₃O | N | |
| H | 2-NH₂ | CH₃O | CH₃O | CH | 141–142° C. |
| H | 2-NH₂ | CH₃O | CH₃O | N | |
| Cl | 5-NH₂ | CH₃O | CH₃ | N | |
| CH₃O | 5-NH₂ | CH₃O | CH₃ | CH | |
| F | 5-NH₂ | CH₃O | CH₃ | N | |
| Br | 5-NH₂ | C₂H₅O | CH₃O | CH | |
| CH₃ | 5-NH₂ | CH₃O | CH₃ | N | 204–213° C. |
| CH₃ | 5-NH₂ | CH₃O | CH₃O | CH | 104–106° C. |
| H | 3-NH₂ | CH₃O | CH₃ | CH | |
| H | 3-NH₂ | CH₃O | CH₃O | CH | |
| H | 3-NH₂ | CH₃ | CH₃ | CH | |
| H | 3-NH₂ | CH₃O | CH₃ | N | |
| H | 3-NH₂ | CH₃O | CH₃O | N | |
| Cl | 5-NH₂ | CH₃O | CH₃O | CH | |
| Cl | 5-Nh₂ | CH₃O | CH₃ | CH | |
| CH₃ | 5-NH₂ | CH₃O | CH₃ | CH | 135–137° C. |
| CH₃ | 5-NH₂ | C₂H₅O | CH₃ | CH | |
| H | 2-NH₂ | CH₃ | CH₃ | N | |
| H | 2-NH₂ | CH₃ | CH₃ | CH | |
| H | 2-NH₂ | CH₃ | CH₃O | CH | |
| CH₃ | 5-NH₂ | CH₃O | CH₃O | N | 205–212° C. |
| CH₃ | 5-NH₂ | C₂H₅O | CH₃O | CH | |
| CH₃ | 5-NH₂ | C₂H₅O | CH₃ | N | |
| Cl | 5-NH₂ | C₂H₅O | CH₃ | N | |
| Cl | 5-NH₂ | C₂H₅O | CH₃ | CH | |
| Cl | 5-NH₂ | C₂H₅O | CH₃O | CH | |
| C₂H₅ | 5-NH₂ | OCH₃ | CH₃ | CH | |
| CH(CH₃)₂ | 5-NH₂ | OCH₃ | CH₃ | CH | |
| CH₂CH₂CH₃ | 5-NH₂ | OCH₃ | CH₃ | CH | |
| SO₂CH₃ | 5-NH₂ | OCH₃ | CH₃ | CH | |
| SO₂CH₂CH₃ | 5-NH₂ | OCH₃ | CH₃ | CH | |
| SO₂CH(CH₃)₂ | 5-NH₂ | OCH₃ | CH₃ | CH | |
| SO₂CH₂CH₂CH₃ | 5-NH₂ | OCH₃ | CH₃ | CH | |
| SO₂CH₃ | 5-NH₂ | OCH₃ | OCH₃ | CH | |
| SO₂CH₂CH₃ | 5-NH₂ | OCH₃ | OCH₃ | CH | |
| SO₂CH₂CH₂CH₃ | 5-NH₂ | OCH₃ | OCH₃ | CH | |
| C₂H₅ | 5-NH₂ | OCH₃ | CH₃ | N | |
| CH₂CH₂CH₃ | 5-NH₂ | OCH₃ | CH₃ | N | |
| CH(CH₃)₂ | 5-NH₂ | OCH₃ | CH₃ | N | |
| SO₂CH₃ | 5-NH₂ | OCH₃ | CH₃ | N | |
| SO₂C₂H₅ | 5-NH₂ | OCH₃ | CH₃ | N | |
| SO₂CH₂CH₂CH₃ | 5-NH₂ | OCH₃ | CH₃ | N | |
| SO₂CH(CH₃)₂ | 5-NH₂ | OCH₃ | CH₃ | N | |

In accordance with the technique described by and for Equation 6, amido compounds of this invention can be prepared. For example, the compound of Example 7 can be converted to 2-acetamido-N-[(4-methoxy-6-methylpyrimidin-2-yl)aminocarbonyl]benzenesulfonamide as follows.

To a solution of 3.4 g of 2-amino-N-[(4-methoxy-6-methylpyrimidin-2-yl)aminocarbonyl]benzenesulfonamide in 200 ml of methylene chloride is added a solution prepared from 0.9 g of acetyl chloride, 0.9 g of pyridine, and 25 ml of methylene chloride. After stirring at ambient temperature for two days, the reaction mixture is worked with an equal volume of water several times, dried over magnesium sulfate, filtered and concentrated to yield the desired compound, 2-acetamido-N-[(4-methoxy-6-methylpyrimidin-2-yl)aminocarbonyl]benzenesulfonamide, which can be used without further purification for the purposes of this invention.

The compound of Example 7 can also be converted to 2-acetamido-N-[(4-methoxy-6-methylpyrimidin-2-yl)aminocarbonyl]benzenesulfonamide by the method described in Equation 7A as shown in Example 8. By using equivalent amounts of other appropriate aminobenzenesulfonamides additional compounds of Formula I set forth in Table V can be prepared according to the method of Example 8.

EXAMPLE 8

2-Acetamido-N-[(4-methoxy-6-methylpyrimidin-2-yl)aminocarbonyl]benzenesulfonamide 2-Amino-N-[(4-methoxy-6-methylpyrimidin-2-yl)aminocarbonyl]benzenesulfonamide (1.0 g) suspended in 25 ml of dichloromethane was treated with ketene for 10 minutes (ca. 0.4 mole/hr). The mixture was allowed to stand and after 15 minutes a light orange solution resulted. Evaporation of the solvent gave an orange glassy oil which was triturated with water and allowed to stand for 16 hours. The white solid thus obtained was removed by filtration and dried in-vacuo to yield 0.24 g of the desired product, m.p. 161°–162°. The product showed absorption peaks by proton NMR at 4.0 (singlet, 3H); 2.5 (singlet, 3H) and 2.1 (singlet, 3H) consistent for the acetylated derivative. The infrared absorption spectrum showed peaks at 1700, 1695, 1610 and 1580 also confirming the desired acylation.

By using equivalent amounts of an appropriate aminobenzenesulfonamide and an appropriate anhydride, the compounds of Formula I set forth in Table V can be prepared in accordance with the procedure described by and for Equation 7. For example, 5-acetamido-2-chloro-N-[(4-methoxy-6-methyl-1,3,5-triain-3-yl)aminocarbonyl]benzenesulfonamide can be prepared as follows.

To a solution of 37.3 g of 5-amino-2-chloro-N-[(4-methoxy-6-methyl-1,3,5-triazin-2-yl)aminocarbonyl]-benzenesulfonamide prepared in a minimum amount of boiling chloroform, is added with vigorous stirring 20.4 g of acetic anhydride. The resulting mixture is then refluxed for 24 hours, the chloroform, excess acetic anhydride and acetic acid are removed in vacuo to yield as residue the desired product, 5-acetamido-2-chloro-N-[(4-methoxy-6-methyl-1,3,5-triazin-2-yl)aminocarbonyl]benzenesulfonamide.

TABLE V

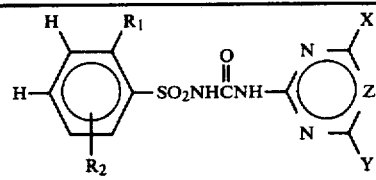

| $R_1$ | $R_2$ | X | Y | Z | m.p. |
|---|---|---|---|---|---|
| H | 3-NHCOCH$_3$ | OCH$_3$ | OCH$_3$ | CH | |
| H | 3-NHCOCH$_3$ | OCH$_3$ | OCH$_3$ | N | |
| H | 3-NHCOCH$_3$ | OCH$_3$ | CH$_3$ | N | |
| H | 3-NHCOC$_2$H$_5$ | OC$_2$H$_5$ | CH$_3$ | N | |
| Cl | 5-NHCOCH$_3$ | OCH$_3$ | OCH$_3$ | CH | |
| Cl | 5-NHCOC$_2$H$_5$ | OCH$_3$ | OCH$_3$ | N | |
| Cl | 5-NHCOCH$_3$ | OCH$_3$ | CH$_3$ | N | |
| Cl | 5-NHCOCH$_3$ | OC$_2$H$_5$ | CH$_3$ | N | |
| CH$_3$ | 5-NHCOC$_2$H$_5$ | OCH$_3$ | OCH$_3$ | CH | |
| CH$_3$ | 5-NHCOCH$_3$ | OCH$_3$ | OCH$_3$ | N | |
| CH$_3$ | 5-NHCOCH$_3$ | OCH$_3$ | CH$_3$ | N | |
| CH$_3$ | 5-NHCOCH$_3$ | OC$_2$H$_5$ | CH$_3$ | N | |
| Br | 5-NHCOC$_2$H$_5$ | OCH$_3$ | OCH$_3$ | CH | |
| Br | 5-NHCOCH$_3$ | OCH$_3$ | OCH$_3$ | N | |
| Br | 5-NHCOCH$_3$ | OCH$_3$ | CH$_3$ | N | |
| Br | 5-NHCOCH$_3$ | OC$_2$H$_5$ | CH$_3$ | N | |
| F | 5-NHCOC$_2$H$_5$ | OC$_2$H$_5$ | OCH$_3$ | CH | |
| F | 5-NHCOC$_2$H$_5$ | OCH$_3$ | OCH$_3$ | N | |
| F | 5-NHCOC$_2$H$_5$ | OCH$_3$ | CH$_3$ | N | |
| F | 5-NHCOCH$_3$ | OC$_2$H$_5$ | OCH$_3$ | N | |
| OCH$_3$ | 5-NHCOCH$_3$ | OCH$_3$ | OCH$_3$ | CH | |
| OCH$_3$ | 5-NHCOCH$_3$ | OCH$_3$ | OCH$_3$ | N | |
| OCH$_3$ | 5-NHCOCH$_3$ | OCH$_3$ | CH$_3$ | N | |
| OCH$_3$ | 5-NHCOCH$_3$ | OC$_2$H$_5$ | OCH$_3$ | N | |
| NO$_2$ | 5-NHCOCH$_3$ | OCH$_3$ | OCH$_3$ | CH | |
| NO$_2$ | 5-NHCOCH$_3$ | OCH$_3$ | OCH$_3$ | N | |
| NO$_2$ | 5-NHCOCH$_3$ | OCH$_3$ | CH$_3$ | N | |
| NO$_2$ | 5-NHCOCH$_3$ | OC$_2$H$_5$ | OCH$_3$ | N | |
| H | 2-NHCO(n-C$_3$H$_7$) | OCH$_3$ | OCH$_3$ | CH | |
| H | 2-NHCO(n-C$_3$H$_7$) | OCH$_3$ | CH$_3$ | N | |
| H | 3-NHCO(n-C$_3$H$_7$) | OC$_2$H$_5$ | CH$_3$ | N | |
| Cl | 5-NHCO(n-C$_3$H$_7$) | OCH$_3$ | OCH$_3$ | CH | |
| Cl | 5-NHCO(n-C$_3$H$_7$) | OCH$_3$ | OCH$_3$ | N | |
| Cl | 5-NHCO(n-C$_3$H$_7$) | OCH$_3$ | CH$_3$ | N | |
| Cl | 5-NHCO(n-C$_3$H$_7$) | OC$_2$H$_5$ | CH$_3$ | N | |
| CH$_3$ | 5-NHCO(n-C$_3$H$_7$) | OCH$_3$ | OCH$_3$ | CH | |
| CH$_3$ | 5-NHCO(n-C$_3$H$_7$) | OCH$_3$ | OCH$_3$ | N | |
| Br | 5-NHCO(n-C$_3$H$_7$) | OC$_2$H$_5$ | CH$_3$ | CH | |
| Br | 5-NHCO(n-C$_3$H$_7$) | OCH$_3$ | CH$_3$ | N | |
| F | 5-NHCO(n-C$_3$H$_7$) | OCH$_3$ | OCh$_3$ | CH | |
| F | 5-NHCO(n-C$_3$H$_7$) | OC$_3$H$_5$ | CH$_3$ | N | |
| OCH$_3$ | 5-NHCO(n-C$_3$H$_7$) | OCH$_3$ | CH$_3$ | CH | |
| OCH$_3$ | 5-NHCO(n-C$_3$H$_7$) | OC$_2$H$_5$ | CH$_3$ | N | |
| NO$_2$ | 5-NHCO(n-C$_3$H$_7$) | OCH$_3$ | OCH$_3$ | CH | |
| NO$_2$ | 5-NHCO(n-C$_3$H$_7$) | OCH$_3$ | OCH$_3$ | N | |
| C$_2$H$_5$ | 5-NHCOCH$_3$ | CH$_3$ | OCH$_3$ | CH | |
| CH(CH$_3$)$_2$ | 5-NHCOCH$_3$ | CH$_3$ | OCH$_3$ | CH | |
| CH$_2$CH$_2$CH$_3$ | 5-NHCOCH$_3$ | CH$_3$ | OCH$_3$ | CH | |
| SO$_2$CH$_3$ | 5-NHCOCH$_3$ | CH$_3$ | OCH$_3$ | CH | |
| SO$_2$CH$_2$CH$_3$ | 5-NHCOCH$_3$ | CH$_3$ | OCH$_3$ | CH | |
| SO$_2$CH$_2$CH$_2$CH$_3$ | 5-NHCOCH$_3$ | CH$_3$ | OCH$_3$ | CH | |
| SO$_2$CH$_3$ | 5-NHCOCH$_3$ | OCH$_3$ | OCH$_3$ | CH | |
| SO$_2$CH$_2$CH$_3$ | 5-NHCOCH$_3$ | OCH$_3$ | OCH$_3$ | CH | |
| SO$_2$CH(CH$_3$)$_2$ | 5-NHCOCH$_3$ | OCH$_3$ | OCH$_3$ | CH | |
| C$_2$H$_5$ | 3-NHCOCH$_3$ | CH$_3$ | OCH$_3$ | N | |
| CH(CH$_3$)$_2$ | 5-NHCOCH$_3$ | CH$_3$ | OCH$_3$ | N | |
| CH$_2$CH$_2$CH$_3$ | 3-NHCOCH$_3$ | CH$_3$ | OCH$_3$ | N | |
| SO$_2$CH$_3$ | 5-NHCOCH$_3$ | CH$_3$ | OCH$_3$ | N | |
| SO$_2$CH$_2$CH$_3$ | 5-NHCOCH$_3$ | CH$_3$ | OCH$_3$ | N | |
| SO$_2$CH$_2$CH$_2$CH$_3$ | 5-NHCOCH$_3$ | CH$_3$ | OCH$_3$ | N | |
| SCH$_3$ | 5-NHCOCH$_3$ | CH$_3$ | OCH$_3$ | N | |
| SCH$_2$CH$_3$ | 5-NHCOCH$_3$ | CH$_3$ | OCH$_3$ | N | |
| SCH(CH$_3$)$_2$ | 5-NHCOCH$_3$ | CH$_3$ | OCH$_3$ | N | |
| H | 2-NHCOCH$_3$ | CH$_3$ | CH$_3$ | CH | |

TABLE V-continued

Structure: benzene ring with H, H, R₁, R₂ substituents, SO₂NHC(=O)NH- linked to a 6-membered ring with N, N, X, Y, Z positions.

| R₁ | R₂ | X | Y | Z | m.p. |
|---|---|---|---|---|---|
| H | 2-NHCOCH₃ | CH₃ | OCH₃ | CH | 161–162° C. |
| H | 2-NHCOCH₃ | OCH₃ | OCH₃ | CH | |
| H | 2-NHCOCH₃ | CH₃ | CH₃ | N | |
| H | 2-NHCOCH₃ | CH₃ | OCH₃ | N | |
| H | 2-NHCOCH₃ | OCH₃ | OCH₃ | N | |

By using the procedure of Equation 8 or 12 with equivalent amounts of an appropriate aminobenzenesulfonamide and an appropriate carbamoyl halide or chloroformate, and compounds of Formula I as set forth in Table VI can be prepared. For example, 2-dimethylureido-N-[(4-methoxy-6-methyl-1,3,5-triazin-2-yl)aminocarbonyl]benzenesulfonamide can be prepared as follows.

A mixture containing 0.8 g of dimethylcarbamoyl chloride and 0.8 g of pyridine is warmed to 80° on a steam bath for twenty minutes and then diluted to 25 ml with methylene chloride. The above mixture is then added to 200 ml of methylene chloride containing 3.3 g of 2-amino-N-[(4-methoxy-6-methyl-1,3,5-triazin-2-yl)aminocarbonyl]benzenesulfonamide. The mixture is stirred at reflux for one day, then washed thoroughly with ice water, dried over magnesium sulfate, filtered and the solvent distilled off in vacuo to yield the desired product which is sufficiently pure for the purposes of this invention.

TABLE VI

| R₁ | R₂ | X | Y | Z |
|---|---|---|---|---|
| H | 2-NHCO₂CH₃ | C₂H₅O | CH₃ | CH |
| H | 2-NHCO₂CH₃ | CH₃O | CH₃O | CH |
| H | 2-NHCO₂CH₃ | CH₃O | CH₃ | N |
| H | 2-NHCO₂C₂H₅ | CH₃O | CH₃O | N |
| H | 2-NHCO₂C₂H₅ | CH₃O | CH₃ | CH |
| H | 2-NHCO₂C₂H₅ | CH₃O | CH₃ | N |
| H | 2-NHC(=O)SCH₃ | CH₃O | CH₃ | N |
| H | 2-NHC(=O)SCH₃ | CH₃O | CH₃ | CH |
| H | 2-NHC(=O)SCH₃ | CH₃O | CH₃O | CH |
| H | 2-NHC(=O)SC₂H₅ | CH₃O | CH₃O | N |
| H | 2-NHC(=O)SC₂H₅ | CH₃O | CH₃ | N |
| H | 2-NHC(=O)SC₂H₅ | CH₃O | CH₃ | CH |
| H | 2-NHC(=O)N(CH₃)₂ | CH₃O | CH₃O | N |
| H | 2-NHC(=O)N(CH₃)₂ | CH₃O | CH₃ | CH |
| H | 2-NHC(=O)N(CH₃)₂ | C₂H₅O | CH₃O | N |
| H | 2-NHC(=O)N(C₂H₅)₂ | CH₃O | CH₃ | N |
| H | 2-NHC(=O)N(C₂H₅)(CH₃) | CH₃O | CH₃O | CH |
| H | 2-NHC(=O)N(C₂H₅)(CH₃) | CH₃O | CH₃ | CH |
| H | 2-NHC(=O)N(OOCH₃)—CH₃ | CH₃O | CH₃ | N |
| H | 2-NHC(=O)N(OOCH₃)—CH₃ | CH₃O | CH₃O | CH |
| H | 2-NHC(=O)N(OOCH₃)—CH₃ | CH₃O | CH₃ | CH |
| H | 2-NHC(=O)N(OCH₃)(n-C₃H₇)— | CH₃O | CH₃ | CH |
| H | 2-NHC(=O)N(OCH₃)(n-C₃H₇)— | CH₃O | CH₃O | CH |
| H | 2-NHC(=O)N(CH₃)(n-C₄H₉) | CH₃O | CH₃ | N |

TABLE VI-continued

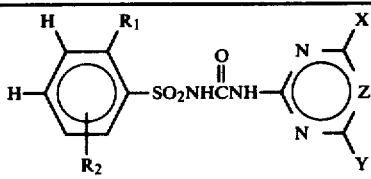

| R₁ | R₂ | X | Y | Z |
|---|---|---|---|---|
| H | 2-NHCS(n-C₃H₇) | CH₃O | CH₃ | N |
| H | 2-NHCO(n-C₃H₇) | CH₃O | CH₃ | CH |
| CH₃ | 5-NHCO₂CH₃ | CH₃ | OCH₃ | CH |
| C₂H₅ | 5-NHCO₂CH₃ | CH₃ | OCH₃ | CH |
| CH₂CH₂CH₃ | 5-NHCO₂CH₃ | CH₃ | OCH₃ | CH |
| SCH₃ | 5-NHCO₂CH₃ | CH₃ | OCH₃ | CH |
| SCH₂CH₃ | 5-NHCO₂CH₃ | CH₃ | OCH₃ | CH |
| SCH₂CH₂CH₃ | 5-NHCO₂CH₃ | CH₃ | OCH₃ | CH |
| SO₂CH₃ | 5-NHCO₂CH₃ | CH₃ | OCH₃ | CH |
| SO₂CH₂CH₃ | 5-NHCO₂CH₃ | CH₃ | OCH₃ | CH |
| SO₂CH₃ | 5-NHCO₂CH₃ | CH₃ | OCH₃ | CH |
| SO₂CH₂CH₃ | 5-NHCO₂CH₃ | CH₃ | OCH₃ | CH |
| Cl | 5-NHCO₂CH₃ | CH₃ | OCH₃ | CH |
| F | 5-NHCO₂CH₃ | CH₃ | OCH₃ | CH |
| Br | 5-NHCO₂CH₃ | CH₃ | OCH₃ | CH |
| CF₃ | 5-NHCO₂CH₃ | CH₃ | OCH₃ | CH |
| NO₂ | 5-NHCO₂CH₃ | CH₃ | OCH₃ | CH |
| OCH₃ | 5-NHCO₂CH₃ | CH₃ | OCH₃ | CH |
| SCH₃ | 5-NHCO₂CH₃ | CH₃ | OCH₃ | N |
| SO₂CH₂CH₂CH₃ | 5-NHCO₂CH₃ | CH₃ | OCH₃ | N |
| SO₂CH₃ | 5-NHCO₂CH₃ | CH₃ | OCH₃ | N |
| SO₂CH₃ | 5-NHCO₂CH₃ | CH₃ | OCH₃ | N |

In addition to the compounds shown in the above table, other compounds which can be prepared according to the same processes are those of Table II and Table III wherein both $R_4$ and $R_5$ are other than hydrogen.

By using the procedure of Equation 9 with equivalent amounts of an appropriate aminobenzenesulfonamide and an appropriate alkyl isocyanate, the compounds of Table VII can be prepared. For example, methyl [2-[[(4-methoxy-6-methyl-1,3,5-triazin-2-yl)aminocarbonyl]aminosulfonyl]phenyl]carbamate can be prepared as follows.

To an anhydrous solution containing 3.4 g of 2-amino-N-[(4-methoxy-6-methyl-1,3,5-triazin-2-yl)aminocarbonyl]benzenesulfonamide and 100 ml of methylene chloride is added 0.6 g of methyl isocyanate with stirring at reflux. The reaction mixture is stirred for an additional sixteen hours at reflux and then concentrated in vacuo to yield the desired compound in sufficient purity for the purposes of this invention.

TABLE VII

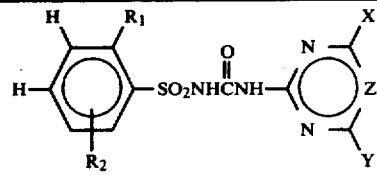

| R₁ | R₂ | X | Y | Z |
|---|---|---|---|---|
| H | 2-NHCNHCH₃ | CH₃ | CH₃ | CH |
| H | 2-NHCNHCH₃ | CH₃O | CH₃O | CH |
| H | 2-NHCNHCH₃ | CH₃O | CH₃ | CH |
| H | 2-NHCNHCH₃ | CH₃O | CH₃O | N |
| H | 2-NHCNHC₂H₅ | CH₃ | CH₃O | CH |
| H | 2-NHCNHC₂H₅ | CH₃O | CH₃O | CH |
| H | 2-NHCNHC₂H₅ | CH₃O | CH₃ | CH |
| H | 2-NHCNH(n-C₃H₇) | CH₃O | CH₃ | CH |
| H | 2-NHCNH(n-C₃H₇) | CH₃O | CH₃ | N |
| H | 2-NHCNH(n-C₃H₇) | CH₃O | CH₃O | N |
| H | 2-NHCNH(i-C₃H₇) | CH₃O | CH₃ | N |
| H | 2-NHCNH(i-C₃H₇) | CH₃O | CH₃ | CH |
| H | 2-NHCNH(n-C₄H₉) | C₂H₅O | CH₃O | CH |
| H | 2-NHCNH(n-C₄H₉) | CH₃O | CH₃ | CH |
| H | 2-NHCNH(n-C₄H₉) | CH₃O | CH₃ | N |
| H | 2-N(CH₃)—C(O)—NHCH₃ | CH₃O | CH₃ | CH |
| H | 2-N(CH₃)—C(O)—NHCH₃ | C₂H₅O | CH₃O | N |
| H | 2-N(CH₃)—C(O)—NHCH₃ | CH₃O | CH₃ | N |
| H | 2-N(CH₃)—CNHC₂H₅ | CH₃O | CH₃ | N |

TABLE VII-continued

Structure:
H, H (phenyl ring with R₁ top, R₂ bottom)—SO₂NHC(=O)NH—pyridine/triazine ring with X, Y, Z

| R₁ | R₂ | X | Y | Z |
|---|---|---|---|---|
| H | CH₃ at 2-N—C(=O)—NHC₂H₅ | CH₃O | CH₃ | CH |
| Cl | 5-NHC(=O)NHCH₃ | OCH₃ | OCH₃ | CH |
| Br | 5-NHC(=O)NHCH₃ | OCH₃ | OCH₃ | CH |
| F | 5-NHC(=O)NHCH₃ | OCH₃ | OCH₃ | CH |
| CF₃ | 5-NHC(=O)NHCH₃ | OCH₃ | OCH₃ | CH |
| OCH₃ | 5-NHC(=O)NHCH₃ | OCH₃ | OCH₃ | CH |
| NO₂ | 5-NHC(=O)NHCH₃ | OCH₃ | OCH₃ | CH |
| CH₃ | 5-NHC(=O)NHCH₃ | OCH₃ | OCH₃ | CH |
| CH(CH₃) | 5-NHC(=O)NHCH₃ | OCH₃ | OCH₃ | CH |
| SCH₃ | 5-NHC(=O)NHCH₃ | OCH₃ | OCH₃ | CH |
| SO₂CH₃ | 5-NHC(=O)NHCH₃ | CH₃ | OCH₃ | CH |
| SO₂CH₃ | 5-NHC(=O)NHCH₃ | OCH₃ | OCH₃ | CH |
| SCH(CH₃)₂ | 5-NHC(=O)NHCH₃ | OCH₃ | OCH₃ | CH |
| SO₂CH₂CH₃ | 5-NHC(=O)NHCH₃ | OCH₃ | OCH₃ | CH |
| SO₂CH₂CH₂CH₃ | 5-NHC(=O)NHCH₃ | OCH₃ | OCH₃ | CH |
| CH(CH₃)₂ | 5-NHC(=O)NHCH₃ | OCH₃ | CH₃ | N |
| SCH₃ | 5-NHC(=O)NHCH₃ | OCH₃ | OCH₃ | N |
| SO₂CH₃ | 5-NHC(=O)NHCH₃ | OCH₃ | CH₃ | N |
| SO₂CH₂CH₂CH₃ | 5-NHC(=O)NHCH₃ | OCH₃ | CH₃ | N |
| SO₂CH₂CH₃ | 5-NHC(=O)NHCH₃ | OCH₃ | CH₃ | N |

By using the procedure of Equation 10 with equivalent amounts of an appropriate aminobenzenesulfonamide and an appropriate aldehyde, the compounds of Table VIII can be prepared. For example, 5-dimethylamino-2-chloro-N-[(4-methoxy-6-methyl-1,3,5,-triazin-2-yl)aminocarbonyl]benzenesulfonamide can be prepared as follows.

To an agitated solution of 3.7 g of 5-amino-2-chloro-N-[(4-methoxy-6-methyl-1,3,5-triazin-2-yl)aminocarbonyl]benzenesulfonamide and 0.88 g of sodium cyanoborohydride in 50 ml of acetonitrile is added 3 ml of formalin. To the reaction mixture is then added 1 ml of glacial acetic acid over a period of 10 minutes. The reaction is then stirred at room temperature for 2 hours, another ml of glacial acetic acid is added and stirring is continued for an additional 30 minutes. The reaction mixture is then poured into 50 ml of water, brought to pH 7 by the addition of aqueous sodium hydroxide and extracted several times with methylene chloride. The combined methylene chloride extracts are washed with brine and dried over anhydrous magnesium sulfate. Evaporation of the solvent in vacuo yields the desired product, 5-dimethylamino-2-chloro-N-[(4-methoxy-6-methyl-1,3,5-triazin-2-yl)aminocarbonyl]benzenesulfonamide.

TABLE VIII

| R₁ | R₂ | X | Y | Z |
|---|---|---|---|---|
| H | 2-N(CH₃)₂ | OCH₃ | OCH₃ | CH |
| H | 2-N(CH₃)₂ | OCH₃ | OCH₃ | N |
| H | 2-N(CH₃)₂ | OCH₃ | CH₃ | N |
| H | 3-N(CH₃)₂ | OC₂H₅ | CH₃ | N |
| Cl | 5-N(CH₃)₂ | OCH₃ | OCH₃ | CH |
| Cl | 5-N(CH₃)₂ | OCH₃ | CH₃ | N |
| Cl | 5-N(CH₃)₂ | OCH₃ | OCH₃ | N |
| Cl | 5-N(CH₃)₂ | OC₂H₅ | CH₃ | N |
| Br | 5-N(CH₃)₂ | OCH₃ | CH₃ | CH |
| Br | 5-N(CH₃)₂ | OCH₃ | CH₃ | N |
| Br | 5-N(CH₃)₂ | OCH₃ | OCH₃ | N |
| Br | 5-N(CH₃)₂ | OC₂H₅ | CH₃ | N |
| F | 5-N(CH₃)₂ | OCH₃ | OCH₃ | N |
| OCH₃ | 5-N(CH₃)₂ | OCH₃ | CH₃ | CH |
| OCH₃ | 5-N(CH₃)₂ | OCH₃ | OCH₃ | N |
| OCH₃ | 5-N(CH₃)₂ | OCH₃ | CH₃ | N |
| H | 3-N(CH₃)₂ | OCH₃ | CH₃ | CH |
| H | 3-N(CH₃)₂ | OC₂H₅ | OCH₃ | CH |
| H | 3-N(CH₃)₂ | CH₃ | CH₃ | CH |

TABLE VIII-continued

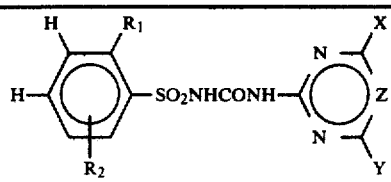

| R₁ | R₂ | X | Y | Z |
|---|---|---|---|---|
|  | 3-N(CH₃)₂ | OCH₃ | CH₃ | N |
| O₂ | 5-N(CH₃)₂ | OCH₃ | OCH₃ | CH |
| O₂ | 5-N(CH₃)₂ | OCH₃ | OCH₃ | N |
| O₂ | 5-N(CH₃)₂ | OCH₃ | CH₃ | N |
| O₂ | 5-N(CH₃)₂ | OC₂H₅ | CH₃ | N |
|  | 2-N(CH₃)₂ | CH₃ | CH₃ | N |
|  | 2-N(CH₃)₂ | CH₃O | CH₃ | CH |
|  | 2-N(CH₃)₂ | CH₃ | CH₃ | CH |
| H₃ | 5-N(CH₃)₂ | OCH₃ | OCH₃ | CH |
| H₃ | 5-N(CH₃)₂ | OCH₃ | OCH₃ | N |
| H₃ | 5-N(CH₃)₂ | OCH₃ | CH₃ | N |
| H₃ | 5-N(CH₃)₂ | OC₂H₅ | CH₃ | N |
|  | 3-N(n-C₂H₅)₂ | OCH₃ | CH₃ | N |
|  | 5-N(n-C₃H₇)₂ | OCH₃ | OCH₃ | CH |
|  | 5-N(n-C₂H₅)₂ | OCH₃ | OCH₃ | N |
|  | 5-N(n-C₃H₇)₂ | OCH₃ | CH₃ | N |
|  | 5-N(n-C₃H₇)₂ | OC₂H₅ | CH₃ | N |
|  | 5-N(n-C₂H₅)₂ | OCH₃ | CH₃ | CH |
|  | 5-N(n-C₃H₇)₂ | OCH₃ | CH₃ | N |
|  | 5-N(n-C₃H₇)₂ | OC₂H₅ | CH₃ | N |
| H₃ | 5-N(n-C₂H₅)₂ | OCH₃ | OCH₃ | CH |
| H₃ | 5-N(n-C₃H₇)₂ | OCH₃ | CH₃ | N |
| H₃ | 5-N(n-C₃H₇)₂ | OC₂H₅ | CH₃ | N |
|  | 5-N(n-C₃H₇)₂ | OC₂H₅ | OCH₃ | N |
| CH₃ | 5-N(n-C₃H₇)₂ | OCH₃ | CH₃ | CH |
| CH₃ | 5-N(n-C₃H₇)₂ | OCH₃ | OCH₃ | N |
| CH₃ | 5-N(n-C₂H₅)₂ | OC₂H₅ | OCH₃ | N |
| O₂ | 5-N(n-C₃H₇)₂ | OCH₃ | OCH₃ | CH |
| O₂ | 5-N(n-C₃H₇)₂ | OCH₃ | OCH₃ | N |
| O₂ | 5-N(n-C₃H₇)₂ | OC₂H₅ | OCH₃ | N |
|  | 3-NHCH₃ | OCH₃ | OCH₃ | CH |
|  | 3-NHCH₃ | OCH₃ | CH₃ | N |
|  | 3-NHC₂H₅ | OCH₃ | CH₃ | N |
|  | 5-NHCH₃ | OCH₃ | CH₃ | CH |
|  | 5-NHC₂H₅ | OCH₃ | OCH₃ | N |
|  | 5-NHCH₃ | OCH₃ | CH₃ | N |
|  | 5-NHCH₃ | OC₂H₅ | CH₃ | N |
|  | 5-NHCH₃ | OCH₃ | CH₃ | CH |
|  | 5-NHC₂H₅ | OCH₃ | OCH₃ | N |
|  | 5-NHC₃H₇ | OC₂H₅ | CH₃ | N |
| H₃ | 5-NHCH₃ | OCH₃ | OCH₃ | CH |
| H₃ | 5-NHCH₃ | OCH₃ | CH₃ | N |
| H₃ | 5-NHCH₃ | OC₂H₅ | CH₃ | N |
|  | 5-NHCH₃ | OCH₃ | OCH₃ | CH |
|  | 5-NHCH₃ | OCH₃ | CH₃ | N |
|  | 5-NHCH₃ | OC₂H₅ | CH₃ | N |
| CH₃ | 5-NHCH₃ | OCH₃ | OCH₃ | CH |
| CH₃ | 5-NHCH₃ | OCH₃ | CH₃ | N |
| CH₃ | 5-NHCH₃ | OC₂H₅ | CH₃ | N |
| O₂ | 5-NHCH₃ | OCH₃ | CH₃ | N |
| O₂ | 5-NHCH₃ | OCH₃ | CH₃ | CH |
| O₂ | 5-NHCH₃ | OC₂H₅ | CH₃ | N |
| ₂H₅ | 5-NHCH₃ | OCH₃ | OCH₃ | CH |
| H(CH₃)₂ | 5-NHCH₃ | OCH₃ | OCH₃ | CH |
| ₂H₃ | 5-NHCH₃ | OCH₃ | OCH₃ | CH |
| )₂CH₃ | 5-NHCH₃ | OCH₃ | OCH₃ | CH |
| )₂CH₂CH₂CH₃ | 5-NHCH₃ | OCH₃ | OCH₃ | CH |
| )₂CH(CH₃)₂ | 5-NHCH₃ | OCH₃ | OCH₃ | CH |
| ₂H₅ | 5-N(CH₃)₂ | OCH₃ | CH₃ | N |
| H₂CH₂CH₃ | 5-N(CH₃)₂ | OCH₃ | CH₃ | N |
| )₂CH₃ | 5-N(CH₃)₂ | OCH₃ | CH₃ | N |
| )₂CH₂CH₂CH₃ | 5-N(CH₃)₂ | OCH₃ | CH₃ | N |
| )₂CH₃ | 5-N(CH₃)₂ | OCH₃ | CH₃ | N |

By using the procedure of Equation 11 with equivalent amounts of an appropriate benzenesulfonyl isocyanate and an appropriate 2-aminopyrimidine or 2-amino-3,5-triazine, the compounds of Table IX can be prepared. For example, 2-chloro-[(4-methoxy-6-methyl-pyrimidin-2-yl)aminocarbonyl]-5-pyrrolidinobenzenesulfonamide can be prepared as follows.

To a suspension of 1.4 g of 2-amino-4-methoxy-6-methylpyrimidine in 50 ml of methylene chloride is added with stirring 2.9 g of 2-chloro-5-pyrrolidinobenzenesulfonyl isocyanate dissolved in 25 ml of methylene chloride at ambient temperature and pressure. After stirring overnight, the solvent is removed in vacuo. The residue thus obtained is the desired 2-chloro-[(4-methoxy-6-methylpyrimidin-2-yl)aminocarbonyl]-5-pyrrolidinobenzenesulfonamide which may be used for the purposes of this invention without further purification. Its purity can be improved by trituration with butyl chloride and filtration.

TABLE IX

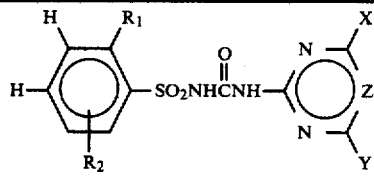

| R₁ | R₂ | X | Y | Z |
|---|---|---|---|---|
| H | 3-N⟨pyrrolidine⟩ | CH₃O | CH₃ | CH |
| H | 3-N⟨pyrrolidine⟩ | CH₃O | CH₃O | CH |
| H | 3-N⟨pyrrolidine⟩ | CH₃O | CH₃ | N |
| H | 3-N⟨morpholine⟩ | CH₃O | CH₃O | N |
| H | 3-N⟨morpholine⟩ | CH₃O | CH₃ | N |
| H | 3-N⟨piperidine⟩ | CH₃O | CH₃ | CH |
| Cl | 5-N⟨pyrrolidine⟩ | CH₃O | CH₃ | N |
| Cl | 5-N⟨pyrrolidine⟩ | CH₃O | CH₃ | CH |
| Cl | 5-N⟨pyrrolidine⟩ | CH₃O | CH₃O | CH |

TABLE IX-continued

Structure: benzene ring with H, R₁ (ortho positions), SO₂NHC(O)NH- linked to a 6-membered N-heterocycle with X, Y, Z substituents; R₂ on benzene.

| R₁ | R₂ | X | Y | Z |
|---|---|---|---|---|
| CH₃ | 5-N morpholino | CH₃O | CH₃ | N |
| CH₃ | 5-N morpholino | CH₃O | CH₃ | CH |
| CH₃O | 5-N pyrrolidinyl | CH₃O | CH₃ | N |
| CH₃O | 5-N pyrrolidinyl | CH₃O | CH₃ | CH₃ |
| NO₂ | 3-N piperidinyl | CH₃O | CH₃ | CH |
| NO₂ | 3-N morpholino | CH₃O | CH₃O | N |
| NO₂ | 3-N pyrrolidinyl | CH₃O | CH₃ | N |
| C₂H₅ | 5-N pyrrolidinyl | OCH₃ | OCH₃ | CH |
| CH(CH₃)₂ | 5-N pyrrolidinyl | OCH₃ | OCH₃ | CH |
| SO₂CH₃ | 5-N pyrrolidinyl | OCH₃ | OCH₃ | CH |
| SCH₃ | 5-N pyrrolidinyl | OCH₃ | OCH₃ | CH |
| SO₂CH₃ | 5-N pyrrolidinyl | CH₃ | OCH₃ | CH |
| SO₂CH₂CH₂CH₃ | 5-N pyrrolidinyl | OCH₃ | OCH₃ | CH |
| SO₂CH₃ | 5-N pyrrolidinyl | CH₃ | OCH₃ | N |
| SO₂CH₂CH₂CH₃ | 5-N pyrrolidinyl | CH₃ | OCH₃ | N |
| SO₂CH₂CH₂CH₃ | 5-N pyrrolidinyl | OCH₃ | OCH₃ | N |
| SO₂CH₃ | 5-N pyrrolidinyl | OCH₃ | OCH₃ | N |
| SCH₃ | 5-N pyrrolidinyl | CH₃ | OCH₃ | N |
| CH(CH₃)₂ | 5-N pyrrolidinyl | CH₃ | OCH₃ | N |
| CH₂CH₃ | 5-N pyrrolidinyl | CH₃ | OCH₃ | N |

Additional compounds wherein R₆ and R₇ are both other than hydrogen, which can be prepared by this method are shown in Table VIII.

EXAMPLE 9

2-Amino-N-[(4-methoxy-6-methyl-2-pyrimidinyl)aminocarbonyl]benzenesulfonamide—Sodium salt To a suspension of 50 mg of 2-amino-N-[(4-methoxy-6-methyl-2-pyrimidinyl)aminocarbonyl]benzenesulfonamide in 3 ml of methanol was added a solution of 10 mg of sodium methoxide in 2 ml of methanol. The resulting clear solution was gently heated on a steam bath for 5 minutes and the solvent removed in vacuo to yield a glass. Trituration with 5 ml of ethylacetate followed by gentle heating and filtration yields the sodium salt of 2-amino-N-[(4-methoxy-6-methyl-2-pyrimidinyl)aminocarbonyl]benzenesulfonamide, m.p. 224–225 (dec.).

Following the procedure given in Example 9 the compounds in Table X can be prepared.

TABLE X $$\left[ \text{Ar-SO}_2\text{N-CNH-} \underset{\substack{\text{N} \\ \text{Y}}}{\overset{\substack{\text{X} \\ \text{N} \\ \text{Z}}}{}} \right]_n M^{\oplus n}$$

(with R$_1$, R$_2$ on benzene ring)

| R$_1$ | R$_2$ | X | Y | Z | M$^+$ | n |
|---|---|---|---|---|---|---|
| NH$_2$ | H | CH$_3$ | OCH$_3$ | CH | Na | 1 |
| NH$_2$ | H | CH$_3$ | CH$_3$ | CH | Na | 1 |
| NH$_2$ | H | CH$_3$ | OCH$_3$ | N | K | 1 |
| NH$_2$ | H | CH$_3$ | OCH$_3$ | N | Li | 1 |
| Cl | NH$_2$ | OCH$_3$ | CH$_3$ | CH | K | 1 |
| Cl | NH$_2$ | CH$_3$ | OCH$_3$ | N | Na | 1 |
| Cl | NH$_2$ | OCH$_3$ | OCH$_3$ | N | Na | 1 |
| Cl | NH$_2$ | OCH$_3$ | OCH$_3$ | N | Ca | 2 |
| Cl | NH$_2$ | CH$_3$ | OCH$_3$ | CH | Li | 1 |
| H | NHCO$_2$CH$_3$ | OCH$_3$ | OCH$_3$ | N | Na | 1 |
| H | NHCO$_2$CH$_3$ | OCH$_3$ | OCH$_3$ | N | Ca | 2 |
| H | NHCO$_2$CH$_3$ | OCH$_3$ | CH$_3$ | N | Na | 1 |
| H | NHCO$_2$CH$_3$ | OCH$_3$ | OCH$_3$ | CH | Li | 1 |
| H | NHCO$_2$CH$_3$ | OCH$_3$ | OCH$_3$ | CH | K | 1 |
| H | NHCO$_2$CH$_3$ | OCH$_3$ | CH$_3$ | CH | Na | 1 |
| H | NHCO$_2$CH$_3$ | OCH$_3$ | CH$_3$ | CH | Li | 1 |
| H | NHC(O)NHCH$_3$ | OCH$_3$ | CH$_3$ | CH | Na | 1 |
| H | NHC(O)NHCH$_3$ | CH$_3$ | CH$_3$ | CH | Na | 1 |

TABLE X-continued (structure with R$_1$, R$_2$ on benzene ring — R$_2$ at different position)

| R$_1$ | R$_2$ | X | Y | Z | M$^+$ | n |
|---|---|---|---|---|---|---|
| H | NHC(O)NHCH$_3$ | CH$_3$ | CH$_3$ | CH | Ca | 2 |
| H | NHC(O)NHCH$_3$ | OCH$_3$ | OCH$_3$ | N | K | 1 |

EXAMPLE 10

2-Amino-N-[(4-methoxy-6-methyl-2-pyrimidinyl)aminocarbonyl]benzenesulfonamide—Hydrochloride A suspension of 56 mg of 2-amino-N-[(4-methoxy-6-methyl-2-pyrimidinyl)aminocarbonyl]benzenesulfonamide in 5 ml of ethanolic HCl was gently heated on a steam bath for 5 minutes. The resulting white suspension was evaporated in vacuo to yield the hydrochloride m.p. 154–155 (dec.).

Following the procedure given in Example 10, the compounds of Table XI can be prepared.

TABLE XI $$\left[ \text{structure with NHR}_6\text{R}_7, \text{R}_1 \text{ on benzene, -SO}_2\text{NHCNH-pyrimidinyl} \right]_n A^{n\ominus}$$

| R$_1$ | R$_6$ | R$_7$ | X | Y | Z | A | n |
|---|---|---|---|---|---|---|---|
| H | H | H | CH$_3$ | CH$_3$ | CH | Cl | 1 |
| H | CH$_3$ | CH$_3$ | CH$_3$ | CH$_3$ | CH | Br | 1 |
| H | H | H | CH$_3$ | OCH$_3$ | CH | Cl | 1 |
| H | CH$_3$ | CH$_3$ | CH$_3$ | OCH$_3$ | CH | CCl$_3$CO$_2$ | 1 |
| H | H | H | OCH$_3$ | OCH$_3$ | N | n-C$_{12}$H$_{25}$SO$_3$ | 1 |
| H | H | CH$_3$ | OCH$_3$ | OCH$_3$ | N | Br | 1 |
| H | H | H | CH$_3$ | OCH$_3$ | N | Cl | 1 |
| H | CH$_3$ | H | CH$_3$ | OCH$_3$ | N | p(CH$_3$)C$_2$H$_4$SO$_3$ | 1 |
| Cl | H | H | CH$_3$ | CH$_3$ | CH | Cl | 1 |
| Cl | CH$_3$ | CH$_3$ | CH$_3$ | CH$_3$ | CH | SO$_4$ | 2 |
| Cl | H | H | CH$_3$ | OCH$_3$ | CH | Cl | 1 |
| Cl | H | H | CH$_3$ | CH$_3$ | CH | NO$_3$ | 1 |
| SO$_2$CH$_3$ | H | H | OCH$_3$ | OCH$_3$ | N | n-C$_{12}$H$_{25}$SO$_3$ | 1 |
| SO$_2$CH$_2$CH$_3$ | CH$_3$ | CH$_3$ | OCH$_3$ | OCH$_3$ | N | Br | 1 |
| CH$_2$CH$_3$ | H | H | OCH$_3$ | CH$_3$ | N | HPO$_4$ | 2 |
| CH(CH$_3$)$_2$ | C$_3$H$_7$ | C$_3$H$_7$ | OCH$_3$ | CH$_3$ | N | HSO$_4$ | 1 |
| Cl | CH$_3$ | CH$_3$ | OCH$_3$ | CH$_3$ | N | CCl$_3$CO$_2$ | 1 |
| Br | H | H | CH$_3$ | OCH$_3$ | CH | Cl | 1 |
| Br | C$_2$H$_5$ | C$_2$H$_5$ | CH$_3$ | OCH$_3$ | CH | p(CH$_3$)C$_6$H$_4$SO$_3$ | 1 |
| Br | H | H | CH$_3$ | OCH$_3$ | N | n-C$_{12}$H$_{25}$SO$_3$ | 1 |
| Br | C$_2$H$_5$ | H | CH$_3$ | OCH$_3$ | N | Cl | 1 |
| F | H | H | CH$_3$ | OCH$_3$ | CH | SO$_4$ | 2 |
| F | CH$_3$ | CH$_3$ | CH$_3$ | OCH$_3$ | CH | HSO$_4$ | 1 |
| F | H | H | OCH$_3$ | OCH$_3$ | N | Cl | 1 |
| F | C$_3$H$_7$ | C$_3$H$_7$ | OCH$_3$ | OCH$_3$ | N | CCl$_3$CO$_2$ | 1 |
| CH$_3$ | H | H | CH$_3$ | OCH$_3$ | CH | Cl | 1 |
| CH$_3$ | CH$_3$ | CH$_3$ | CH$_3$ | OCH$_3$ | CH | Br | 1 |
| CH$_3$ | H | H | CH$_3$ | OCH$_3$ | N | n-C$_{12}$H$_{25}$SO$_3$ | 1 |
| CH$_3$ | CH$_3$ | H | CH$_3$ | OCH$_3$ | N | CH$_3$CO$_2$ | 1 |
| CH$_3$ | CH$_3$ | CH$_3$ | CH$_3$ | OCH$_3$ | CH | Br | 1 |
| OCH$_3$ | H | H | CH$_3$ | CH$_3$ | CH | Cl | 1 |
| OCH$_3$ | CH$_3$ | CH$_3$ | CH$_3$ | CH$_3$ | CH | Br | 1 |

TABLE XI-continued $$\left[ \begin{array}{c} \text{structure with } R_1, NHR_6R_7, SO_2NHCNH, X, Y, Z \end{array} \right]^{\oplus} A^{n\ominus}_n$$

| R₁ | R₆ | R₇ | X | Y | Z | A | n |
|---|---|---|---|---|---|---|---|
| OCH₃ | H | H | CH₃ | OCH₃ | N | Cl | 1 |
| OCH₃ | C₂H₅ | C₂H₅ | CH₃ | OCH₃ | N | pCH₃C₆H₄SO₃ | 1 |

EXAMLE 11

2-Amino-N-[(4-methoxy-6-methyl-2-pyrimidinyl)aminocarbonyl]benzenesulfonamide—Triethanolamine salt

To a suspension of 1 g of 2-amino-N-[(4-methoxy-6-methyl-2-pyrimidinyl)aminocarbonyl]benzenesulfonamide in 25 ml of methylene chloride is added 0.44 g of triethanolamine. The solvent is removed under reduced pressure to yield 2-amino-N-[(4-methoxy-6-methyl-2-pyrimidinyl)aminocarbonyl]benzenesulfonamide triethanolammonium salt.

According to the procedure given in Example 11 the compounds in Table XII can be prepared.

| R₁ | R₂ | R₈ | R₉ | R₁₀ | X | Y | Z |
|---|---|---|---|---|---|---|---|
| Cl | 5-NH₂ | C₆H₅ | H | H | OCH₃ | CH₃ | CH |
| H | 2-NHCO₂CH₃ | C₆H₅ | CH₃ | H | OCH₃ | CH₃ | N |
| H | 3-NHCO₂CH₃ | C₆H₅ | CH₃ | CH₃ | OCH₃ | OCH₃ | N |
| NH₂ | H | n-C₁₂H₂₅ | H | H | CH₃ | OCH₃ | N |
| Cl | 5NH₂ | [C₆H₆NH] | | | OCH₃ | CH₃ | N |

TABLE XII $$\left[ \text{structure with } R_1, R_2, SO_2NCNH, X, Y, Z \right]^{\ominus} R_8R_9R_{10}NH^{\oplus}$$

| R₁ | R₂ | R₈ | R₉ | R₁₀ | X | Y | Z |
|---|---|---|---|---|---|---|---|
| NH₂ | H | H | CH₃ | CH₃ | CH₃ | OCH₃ | CH |
| NH₂ | H | H | —CH₂CH₂OH | CH₂CH₂OH | CH₃ | CH₃ | CH |
| NH₂ | H | CH₂CH₂OH | —CH₂CH₂OH | CH₂CH₂OH | CH₃ | OCH₃ | N |
| NH₂ | H | H | H | CH(CH₃)₂ | CH₃ | OCH₃ | N |
| Cl | 5-NH₂ | H | H | H | OCH₃ | CH₃ | CH |
| Cl | 5-NH₂ | H | CH₂CH₂OH | —CH₂CH₂OH | CH₃ | OCH₃ | N |
| Cl | 5-NH₂ | CH₃ | CH₃ | CH₃ | OCH₃ | OCH₃ | N |
| Cl | 5-NH₂ | C₁₂H₂₅ | H | H | OCH₃ | OCH₃ | N |
| Cl | 5-NH₂ | H | CH₃ | CH₃ | CH₃ | OCH₃ | CH |
| H | 2-NHCO₂CH₃ | CH₂CH₂OH | CH₂CH₂OH | OCH₃ | OCH₃ | N | |
| H | 2-NHCO₂CH₃ | C₂H₅ | C₂H₅ | CH₂H₂OH | OCH₃ | OCH₃ | N |
| H | 3-NHCO₂CH₃ | H | CH₃ | CH₃ | OCH₃ | CH₃ | N |
| H | 3-NHCO₂CH₃ | H | H | H | OCH₃ | OCH₃ | CH |
| H | 3-NHCO₂CH₃ | CH₃ | CH₃ | CH₃ | OCH₃ | OCH₃ | CH |
| H | 2-NHCO₂CH₃ | H | H | CH(CH₃)₂ | OCH₃ | CH₃ | CH |
| H | 2-NHCO₂CH₃ | H | CH₃ | CH₃ | OCH₃ | CH₃ | CH |
| H | 2-NHC(O)NHCH₃ | [C₆H₆NH] | | | OCH₃ | CH₃ | CH |
| H | 2-NHC(O)NHCH₃ | CH₃ | CH₃ | CH₃ | CH₃ | CH₃ | CH |

TABLE XII-continued

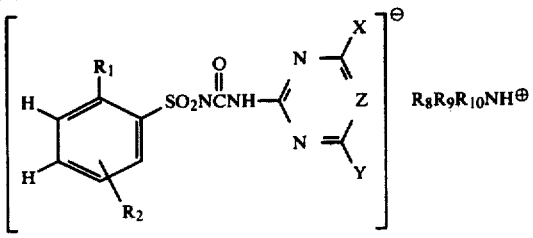

| R$_2$ | R$_8$ | R$_9$ | R$_{10}$ | X | Y | Z |
|---|---|---|---|---|---|---|
| 3-NHCNHCH$_3$ (C=O) | H | C$_2$H$_5$ | C$_2$H$_5$ | CH$_3$ | CH$_3$ | CH |
| 3-NHCNHCH$_3$ (C=O) | C$_{12}$H$_{25}$ | H | H | OCH$_3$ | OCH$_3$ | N |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

TABLE XIII

| | Active Ingredient | Weight Percent* Diluent(s) | Surfactant(s) |
|---|---|---|---|
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 5th Ed., McGraw-Hill, New York, 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley & Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 12

| Wettable Powder | |
|---|---|
| (1-Methylethyl) [3-[[(4-methoxy-6-methylpyrimidin-2-yl)aminocarbonyl]aminosulfonyl]phenyl]-carbamate | 80% |
| sodium alkylnaphthalenesulfonate | 2% |
| sodium ligninsulfonate | 2% |
| synthetic amorphous silica | 3% |

-continued

Wettable Powder

| | |
|---|---|
| kaolinite | 13% |

The ingredients are blended, hammer-milled until all the solids are essentially under 50 microns, reblended, and packaged.

EXAMPLE 13

Wettable Powder

| | |
|---|---|
| 3-(3,3-dimethylureido)-N—[(4-methoxy-6-methylpyrimidin-2-yl)aminocarbonyl]benzenesulfonamide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 14

Granule

| | |
|---|---|
| Wettable Powder of Example 13 | 5% |
| attapulgite granules (U.S.S. 20–40 mesh; 0.84–0.42 mm) | 95% |

A slurry of wettable powder containing 25% solids is sprayed on the surface of attapulgite granules in a double-cone blender. The granules are dried and packaged.

EXAMPLE 15

Extruded Pellet

| | |
|---|---|
| Methyl 3-[[(4-methoxy-6-methylpyrimidin-2-yl)aminocarbonyl]aminosulfonyl]phenyl]carbamate | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 16

Oil Suspension

| | |
|---|---|
| 5-amino-N—[(4,6-dimethoxy-1,3,5-triazin-2-yl)aminocarbonyl]-2-methylbenzenesulfonamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emusified in water.

EXAMPLE 17

Wettable Powder

| | |
|---|---|
| 5-amino-N—[(4,6-dimethoxypyrimidin-2-yl)aminocarbonyl]-2-methylbenzenesulfonamide | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 18

Low Strength Granule

| | |
|---|---|
| 5-amino-N—[(4-methoxy-6-methylpyrimidin-2-yl)aminocarbonyl]-2-methylbenzenesulfonamide | 1% |
| N,N—dimethylformamide | 9% |
| attapulgite granules (U.S.S. 20–40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 19

Aqueous Suspension

| | |
|---|---|
| 5-amino-N—[(4,6-dimethylpyrimidin-2-yl)aminocarbonyl]-2-methylbenzenesulfonamide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 20

Solution

| | |
|---|---|
| 5-amino-N—[(4-methoxy-6-methyl-1,3,5-triazin-2-yl)aminocarbonyl]-2-methylbenzenesulfonamide | 5% |
| water | 95% |

The salt is added directly to the water with stirring to produce the solution, which may then be packaged for use.

EXAMPLE 21

Low Strength Granule

| | |
|---|---|
| 2-Methyl-5-[(methylamino)carbonylamino]-N—[(4-methoxy-6-methypyrimidin-2-yl)aminocarbonyl]benzenesulfonamide | 0.1% |
| attapulgite granules | 99.9% |

-continued

| Low Strength Granule | |
|---|---|
| (U.S.S. 20-40 mesh) | |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 22

| Granule | |
|---|---|
| 2-amino-N—[(4,6-dimethylpyrimidin-2-yl)aminocarbonyl]-benzenesulfonamide | 80% |
| wetting agent | 1% |
| crude ligninsulfonate salt (containing 5-20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14-100 mesh (1410-149 microns), and packaged for use.

EXAMPLE 23

| High Strength Concentrate | |
|---|---|
| 2-amino-N—[(4-methoxy-6-methylpyrimidin-2-yl)aminocarbonyl]benzenesulfonamide | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 24

| Wettable Powder | |
|---|---|
| 2-Methyl-5-[(methylamino)carbonylamino]-N—[(4,6-dimethoxypyrimidin-2-yl)aminocarbonyl]-benzenesulfonamide | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 25

| Wettable Powder | |
|---|---|
| 2-Methyl-5-[(methylamino)carbonylamino]-N—[(4-methoxy-6-methylpyrimidin-2-yl)aminocarbonyl]benzene-sulfonamide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 26

| Oil Suspension | |
|---|---|
| 2-Methyl-5-[(methylamino)carbonylamino]-N—[(4,6-dimethoxypyrimidin-2-yl)aminocarbonyl]-benzenesulfonamide | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 27

| Dust | |
|---|---|
| 5-amino-N—[(4,6-dimethoxy-1,3,5-triazin-2-yl)aminocarbonyl]-2-methylbenzenesulfonamide | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

UTILITY

The compounds of Formula I are useful as herbicides. They may be applied either pre- or post-emergence for the control of undesired vegetation. By properly selecting rate and time of application, compounds of this invention may be used to modify plant growth beneficially.

The precise amount of the compound of Formula I to be used in any given situation will vary according to the particular end result desired, the use involved, the weeds to be controlled, the soil type, the formulation and mode of application, weather conditions, etc. Since so many variables play a role, it is not possible to state a rate of application suitable for all situations. Broadly speaking, the compounds of this invention are used at levels of about 0.1 to 20 kg/ha with a preferred range of 0.2 to 10 kg/ha. The lower rates of the range will generally be selected for lighter soils, for plant growth modification, weed control in crops or in situations in which maximum persistence is not necessary.

The compounds of Formula I may be combined with other herbicides and are particularly useful in combination with 3-(3,4-dichlorophenyl)-1,1-dimethylurea, the triazines such as 2,4-bis(isopropylamino)-6-(methylthio)-s-triazine, the uracils such as 5-bromo-3-sec-butyl-6-methyluracil, N-(phosphonomethyl)glycine, 3- cyclohexyl-1-methyl-6-dimethylamino-s-triazine-2,4-(1H,3H)-dione, N,N-dimethyl-2,2-diphenylacetamide, 2,4-dichlorophenoxyacetic acid (and closely related compounds), 4-amino-6-tert-butyl-3-(methylthio-1,2,4-triazin-5(4H)-one (Lexone®), 3-(3,4-dichlorophenyl)-1-methoxy-1-methylurea (Lorox®), 1,1'-dimethyl-4,4'-bipyridinium ion and monosodium methanearsonate.

The activity of these compounds was discovered in greenhouse tests. The tests are described and the data resulting from them are shown below. It is easily seen from the data that the compounds have utility as herbicides and/or plant growth regulants.

TEST PROCEDURES

Test A

Seeds of crabgrass (Digitaria sp.), barnyardgrass (*Echinochloa crusgalli*), wild oats (*Avena fatua*), Cassia tora, morningglory (Ipomoea sp.), cocklebur (Xanthium sp.), sorghum, corn, soybean, rice, wheat and nutsedge tubers were planted in a growth medium and treated preemergence with the chemicals dissolved in a non-phytotoxic solvent. At the same time, cotton having five leaves (including cotyledonary ones), bush beans with the third trifoliolate leaf expanding, crabgrass with two leaves, barnyardgrass with two leaves, wild oats with one leaf, cassia with three leaves (including cotyledonary ones), morningglory with four leaves (including the cotyledonary ones), cocklebur with four leaves (including the cotyledonary ones), sorghum with three leaves, corn with three leaves, soybean with two cotyledonary leaves, rice with two leaves, wheat with one leaf, and nutsedge with three-five leaves were sprayed. Treated plants and controls were maintained in a greenhouse for 16 days, then all species were compared to controls and visually rated for response to treatment.

Ratings for compounds tested by this procedure are recorded in Table XIV.

0 = no effect
and or 10 = maximum effect
C = chlorosis or necrosis
E = emergence inhibition
G = growth retardation
H = formative effects
S = albinism
U = unusual pigmentation
6Y = abscised buds or flowers
W = wilt
X = axillary stimulation It will be seen that the compounds of Formula I possess excellent herbicidal properties.

TABLE XIV

POST-EMERGENCE

| Structure | Rate kg/ha | Bush Bean | Cotton | Sorghum | Corn | Soybean | Wheat | Wild Oats | Rice | Barnyard-grass | Crab-grass | Morning-glory | Cocklebur | Cassia | Nut-sedge |
|---|---|---|---|---|---|---|---|---|---|---|---|---|---|---|---|
| Structure 1 (m.p. 260° dec) | 2.0 | 5S,7G,6Y | 3C,3H,6G | 7U,9G | 10C | 3C,7H | 9C | 9C | 8C | 10C | 9C | 2C,5H | 3C,8G | 3C | 3G |
| Structure 2 (m.p. 155–159°) | 2.0 | 3C,9G,6Y | 3C,5G | 2C,8G | 2U,8G | 4C,9G | 3C,7G | 3C,8H | 5C,9G | 9H | 7G | 3C,9G | 3C,9G | 8C | 2C,7G |
|  | 0.4 | 6C,9G | 2C,5G | 1C,8G | 9C | 9C | 2C,6G | 1C,6G | 4C,8G | 7H | 1C | 2C,9G | 3C,6G | 3C,6G | 1C,6G |
| Structure 3 (m.p. 147–167°) | 2.0 | 3C,7G,6Y | 2C | 1C,7G | 9H | 3C,8G | 2C,7G | 2C,8H | 3C,8G | 3C | 3G | 2C,7G | 2C,6H | 4C | 5G |
|  | 0.4 | 3C,7G,6Y | 3G | 1C,8G | 3U,8G | 2C,7G,5X | 1C,6G | 7G | 2C,8G | 1C |  | 1C,5G | 1C,2H | 2C | 0 |
| Structure 4 (m.p. 120° dec) | 2.0 | 3S,8G,6Y | 3C,7G | 7U,9G | 9C | 3C,8G | 8C | 9C | 8C | 10C | 9C | 3C,7G | 5C,8G | 5C | 3G |
|  | 0.4 | 3S,7G,6Y | 3C,6G | 7U,8G | 9C | 3C,7G | 9C | 9C | 10C | 10C | 6C,9G | 2C,6G | 1C,8G | 2C | 3G |
| Structure 5 (m.p. 137–145°) | 2.0 | 3C,5G,6Y | 2C | 4G | 5G | 2C,7G | 2G | 2G | 5G | 1C | 0 | 3C | 2C,6H | 3C | 0 |
|  | 0.4 | 2C,6G,6Y | 1C | 4H | 8H | 1C,3H | 2G | 0 | 4G | 0 | 1C | 1C,3H | 2C,7H | 1C | 0 |

Structure 1: OCN–phenyl–SO₂NHCNH(C=O)–[pyrimidine with CH₃ and OCH₃], m.p. 260° dec Structure 2: (CH₃)₂CHOCHN(C=O)–phenyl–SO₂NHCNH(C=O)–[pyrimidine with CH₃ and OCH₃], m.p. 155–159°

Structure 3: (CH₃)₂NCN(C=O)–phenyl–SO₂NHCNH(C=O)–[pyrimidine with CH₃ and OCH₃], m.p. 147–167°

Structure 4: CH₃OCN(C=O)H–phenyl–SO₂NHCNH(C=O)–[pyrimidine with CH₃ and OCH₃], m.p. 120° dec Structure 5: (CH₃)₃CNHCN(C=O)–phenyl–SO₂NHCNH(C=O)–[pyridine with CH₃ and OCH₃], m.p. 137–145°

TABLE XIV-continued

PRE-EMERGENCE

| Structure | Rate kg/ha | Sorghum | Corn | Soybean | Wheat | Wild Oats | Rice | Barnyardgrass | Crabgrass | Morningglory | Cocklebur | Cassia | Nut-sedge |
|---|---|---|---|---|---|---|---|---|---|---|---|---|---|
| OCN-C₆H₄-SO₂NHCNH-pyrimidine(CH₃,OCH₃); m.p. 260° dec | 2.0 | 9G | 9G | 7H | 9G | 2C,8G | 10E | 2C,9H | 2C,8G | 8G | 8G | 8G | 10E |
| (CH₃)₂CHOCHN-C₆H₄-SO₂NHCNH-pyrimidine(CH₃,OCH₃); m.p. 155-159° | 2.0 | 9G | 10E | 9H | 9H | 8G | 10E | 9G | 7G | 9C | 9G | 9G | 10E |
|  | 0.4 | 1C,9G | 9G | 9H | 9G | 8G | 9H | 9G | 4G | 9G | 9G | 8G | 10E |
| (CH₃)₂NCN-C₆H₄-SO₂NHCNH-pyrimidine(CH₃,OCH₃); m.p. 147-167° | 2.0 | 1C,9G | 1C,9G | 8H | 9G | 8G | 10E | 2C,8G | 5G | 9G | 9G | 6G | 9G |
|  | 0.4 | 1C,9G | 2C,9G | 7H | 9G | 1C,7G | 9H | 2C,6G | 2G | 9G | 9G | 5G | 3G |
| CH₃OCN-C₆H₄-SO₂NHCNH-pyrimidine(CH₃,OCH₃); m.p. 120° dec | 2.0 | 1C,9G | 10E | 2H,9H | 1C,9G | 2C,9G | 10E | — | 9C | 8G | 9G | 2C,5G | 10E |
|  | 0.4 | 1C,9G | 9G | 5H | 9G | 9G | 10E | — | 9H | 8G | 9G | 2C,5G | 9G |
| (CH₃)₃CNHCN-C₆H₄-SO₂NHCNH-pyrimidine(CH₃,OCH₃); m.p. 137-145° | 2.0 | 2C | 1C | 1C | 9G | 8G | 10E | 2C,8G | 5G | 9G | 10E | 2C,8G | 7G |
|  | 0.4 | 8G | 1C,8G | 4U | 9G | 8G | 9G | 1C,6G | 4G | 9G | 4G | 7G | 2G |

POST-EMERGENCE

TABLE XIV-continued

| Structure | kg/ha | Bush Bean | Cotton | Morning-glory | Cocklebur | Cassia | Nutsedge | Crab-grass | Barn-yard-grass | Wild Oats | Wheat | Corn | Soybean | Rice | Sorghum |
|---|---|---|---|---|---|---|---|---|---|---|---|---|---|---|---|
| [structure with NH₂, SO₂NHCNH, OCH₃, CH₃ pyrimidine] m.p. 210–215° | 0.4 | 2S,7G,6Y | 2S,2H,7G | 10C | 3H,8G | 2C,7G | 1C,6G | 3C,8G | 10C | 9C | 6C,8H | 5U,9G | 5C,9G | 10C | 5C,9G |
| [structure with NH₂, SO₂NHCNH, CH₃, CH₃ pyrimidine] m.p. 212–216° | 0.4 | 2C,2H,5G | 2C,2H,7G | 1C | 1C,5G | 3G | 4G | 9C | 10C | 5G | 5G | 8H | 0 | 9C | 8H |
| [structure with CH₃, SO₂NHCNH, OCH₃, CH₃ pyrimidine, H₂N] m.p. 204–213° | 0.4 | 7C,9G,6Y | 6C,9G | 9C | 6C,9G | 4C,8G | 2C,8G | 9C | 9C | 9C | 7C,9G | 10C | 6C,9G | 6C,9G | 9C |
| [structure with CH₃, SO₂NHCNH, OCH₃, CH₃ pyrimidine, H₂N] m.p. 132–135° | 0.4 | 8C,9G,6Y | 6C,9G | 9C | 6C,9G | 6C,9G | 2C,8G | 5C,8G | 9C | 9C | 4C,9G | 5U,9C | 5C,9G | 6C,9G | 9C |
| [structure with CH₃, SO₂NHCNH, OCH₃, OCH₃ pyrimidine, H₂N] m.p. 205–212° | 0.4 | 5C,8G,6Y | 6C,9G | 9C | 6C,9G | 3C,3H | 1C,9G | 10C | 9C | 9C | 9C | 10C | 6C,9G | 5C,9G | 9C |

TABLE XIV-continued

TABLE XIV-continued

| Structure | kg/ha | Morningglory | Cocklebur | Cassia | Nutsedge | Crabgrass | Barnyardgrass | Wild Oats | Wheat | Corn | Soybean | Rice | Sorghum |
|---|---|---|---|---|---|---|---|---|---|---|---|---|---|
| CH$_3$-pyrimidine(N, OCH$_3$)-SO$_2$NHCNH-phenyl(CH$_3$)-NH-C(=O)-NHC(CH$_3$)$_3$; m.p. 152–155° | .05 | 2A,6F | 0 | 3G | 0 | 0 | 0 | 2G | 2H | 0 | 0 | 0 | 0 |
| CH$_3$-pyrimidine(N, OCH$_3$)-SO$_2$NHCNH-phenyl(CH$_3$)-NHCNH-CH$_3$; m.p. 175–178° | .05 | 0 | 0 | 0 | 0 | 0 | 2G | 2C,8H | 2C | 1C | 1C,2G | 0 | 8G 2C,8H 0 |

PRE-EMERGENCE

| Structure | kg/ha | Morningglory | Cocklebur | Cassia | Nutsedge | Crabgrass | Barnyardgrass | Wild Oats | Wheat | Corn | Soybean | Rice | Sorghum |
|---|---|---|---|---|---|---|---|---|---|---|---|---|---|
| OCH$_3$/CH$_3$ pyrimidine-SO$_2$NHCNH-phenyl-NH$_2$; m.p. 210–215° | 0.4 | 9G | 10E | 9G | 10E | 9G | 9H | 9H | 9H | 10E | 9H | 10E | 9H |
| CH$_3$/CH$_3$ pyrimidine-SO$_2$NHCNH-phenyl-NH$_2$; m.p. 212–216° | 0.4 | 9G | 8G | 8G | 10E | 7G | 9H | 7G | 7G | 9G | 8H | 8H | 10E |
| OCH$_3$/CH$_3$ pyrimidine-SO$_2$NHCNH-phenyl(CH$_3$)-NH$_2$; m.p. 204–213° | 0.4 | 9G | 9H | 8G | 8G | 3C,9G | 6C,9H | 5C,9H | 4C,9G | 2C,9G | 8H | 10E | 6C,9G |

TABLE XIV-continued

| Structure | | | | | | | | | | | | | |
|---|---|---|---|---|---|---|---|---|---|---|---|---|---|
| Structure with OCH₃, CH₃, SO₂NHCNH, H₂N groups; m.p. 132–135° | 0.4 | 9G | 9H | 5C,9G | 10E | 6C,9G | 7C,9H | 6C,9G | 9H | 10H | 9H | 10E | 6C,9H |
| Structure with OCH₃, OCH₃, CH₃, SO₂NHCNH, H₂N groups; m.p. 205–212° | 0.4 | 9G | 9H | 8G | 4G | 5G | 4C,9H | 2C,7G | 1C,9G | 1C,8G | 8H | 10E | 3C,9H |
| Structure with OCH₃, OCH₃, CH₃, SO₂NHCNH, H₃CNHCNH groups; m.p. 216–218° | 0.05 | 6G | 9H | 8G | 2C,7G | 2C | 3C,9H | 3C,9G | 9G | 1C,9G | 2C,5H | 9H | 5C,9H |
| Structure with OCH₃, CH₃, OCH₃, SO₂NHCNH, H₃CNHCNH groups; m.p. 155–157° | .05 | 3C | 0 | 1C | 0 | 0 | 2C | 1C,5G | 4G | 1C,6G | 2C,3H | 2C, 5G | 2C, 9G |
| Structure with OCH₃, OCH₃, CH₃, SO₂NHCNH, H₂N groups; m.p. 104–106° | 0.4 | 9G | 9H | 2C,9G | 10E | 6C,9G | 9C | 9C | 1C,9G | 1C,9G | 9H | 10E | 5C,9H |

TABLE XIV-continued

| | 0.05 | 1C,5H | 9H | 2C | 1C,8G | 1C,7G | 1C,8G | 1C,9G | 1C,7G | 2C | 2C,8H | 2C,9H |
|---|---|---|---|---|---|---|---|---|---|---|---|---|
| Structure 1 (m.p. 162-164°) | .05 / 1 | 0 / 2G | 0 / 6G | 0 / 3G | 0 / 0 | 0 / 0 | 0 / 0 | 0 / 0 | 0 / 0 | 0 / 0 | 0 / 0 | |
| Structure 2 (m.p. 178-179°) | .05 | 0 | 0 | 0 | 0 | 0 | 0 | 0 | 0 | 0 | 0 | |
| Structure 3 (m.p. 152-155°) | .05 | 0 | 0 | 0 | 0 | 0 | 0 | 0 | 0 | 0 | 0 | 2C |
| Structure 4 (m.p. 175-178°) | | | | | | | | | | | | |
| Structure 5 (m.p. 188-190°) | | | | | | | | | | | | |

TABLE XIV-continued

[Structure 1: 4-methyl-3-(4,6-dimethoxypyrimidin-2-ylaminocarbonylaminosulfonyl)phenyl with NH-C(=O)-NHC(CH₃)₃ substituent]
m.p. 150-152°

[Structure 2: 4-methyl-3-(4,6-dimethoxypyrimidin-2-ylaminocarbonylaminosulfonyl)phenyl with H₃CNHCNH-C(=O)- substituent]
m.p. 147-150°

The above compounds were tested at a low rate and were found to be inactive; it is thought that testing at higher rates would result in herbicidal activity being demonstrated.

Test B

In Test B, plastic pots filled with Fallsington sandy loam were planted to soybeans, cotton, alfalfa, corn, rice, wheat, sorghum, velvetleaf (*Abutilon theophrasti*), sesbania (*Sesbania exaltata*), Cassia (*Cassia tora*), morningglory (Ipomoea spp.), jimsonweed (*Datura stramonium*), cocklebur (*Xanthium pennsylvanicum*), crabgrass (Digitaria spp.), nutsedge (*Cyperus rotundus*), barnyardgrass (*Echinochloa crusgalli*), giant foxtail (*Setaria faberii*) and wild oats (*Avena fatua*). Eighteen days after planting, the young plants and the soil around them were sprayed overall with the test chemical dissolved in a non-phytotoxic solvent. Fourteen days after treatment, all species were compared to untreated controls and visually rated for response to treatment. The ratings are again based on a numerical scale extending from 0=no injury, to 10=complete kill. The ratings for the compound tested by this procedure are presented in Table XV.

TABLE XV

| Compound | Rate kg/ha | Soy-beans | Vel-vet-leaf | Sesbania | Cassia | Cotton | Morn-ing-glory | Alfalfa | Jim-son-weed | Cock-le-bur | Corn | Crab-grass | Rice | Nut-sedge | Barn-yard-grass | Wheat | Giant Fox-tail | Wild Oats | Sor-ghum |
|---|---|---|---|---|---|---|---|---|---|---|---|---|---|---|---|---|---|---|---|
| 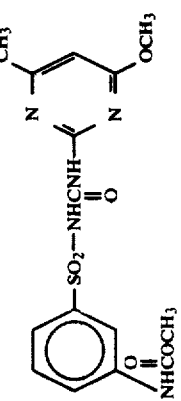 | .25 | 5G,3H | 3G,3H | 0 | 0 | 0 | 0 | 10G,7C,5G | 8G,3C,4G | 7G | 10G,7C,10G,4C | 10G,6C,7G | 10G,4C,8G | 0 | 7C,10G,8G,2C | 10G,2C,10G | 10G,3C,8G | 10G,4C,7G | 10G,4C,2C,10G |
| | .063 | 3G | 0 | 0 | 0 | 0 | 0 | | | 0 | | | | | | | | | |
| 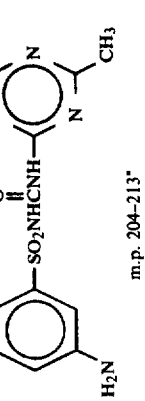 | .25 | 10G,5H | 3H | 0 | 3G | 5G,5H | 6G | 7C,10G,5G | 10G,7C,2H | 5G | 10G,7C,9G,3C | 8G,3C,3G | 10G,4C,8G,3C | 0 | 4C,10G,10G,3C | 10G,3C,10G | 10G,3C,8G | 10G,4C,10G | 8G,3C,10G |
| | .063 | 8G,5H | 0 | 0 | 0 | 2H | 0 | | | 0 | | | | | | | | | |
| 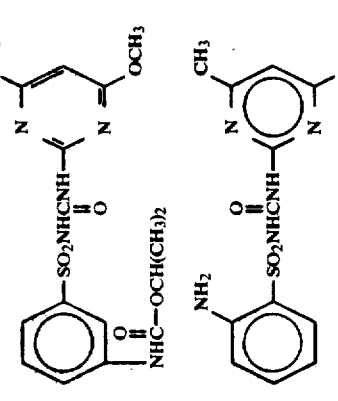 | .25 | 10G,5H | 5G,3H | 8G | 5G | 5G,2H | 7G,3H | 10G,5H,10G,3H | 10G,5C,7G,3H | 8G,3H | 7G,2U,8G | 0 | 10G,4C,8G,3C | 0 | | | | | |
| | .063 | 8G,5H | 0 | 3G | 3G | 0 | 3G,2H | | | 2G | | | | | | | | | |
| 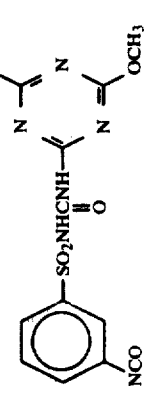 | 0.06 | 9G,3H | 10C | 8G,4C | 8G,2C | 10G,6C,8G,5C | 10G,2C,10G,6C | 10G,6C,10G,9C | 10G,8C,7G,6C | 5G | 9G,2C | 3G | 10G,4C,10G,4C | 5G | 10G,3H,10G,3C | 9G,3G | 7G,10G,5C | 5G,0 | 10G,3H,2G |
| | 0.25 | 10G,3C | — | 10G,7C | 10G,5C | | | | | 7G,3H | | 10G,5H | | 7G | | | | | |
| 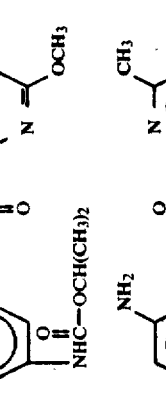 | .03 | 5G,4H | 3G | 5G | 4G | 2G,1C | 8G,4C | 6G,2C | 3G | 0 | 7G,3U | 2G | 8G,3C | 0 | 9C | 5G | 5G | 6G | 8G,2U | m.p. 210–215°  
m.p. 204–213°

Test C

Two plastic bulb pans were filled with fertilized and limed Fallsington silt loam soil. One pan was planted with corn, sorghum, Kentucky bluegrass and several grassy weeds. The other pan was planted with cotton, soybeans, purple nutsedge (*Cyperus rotundus*), and several broadleaf weeds. The following grassy and broadleaf weeds were planted: crabgrass (*Digitaria sanguinalis*), barnyardgrass (*Echinochloa crusgalli*), wild oats (*Avena fatua*), johnsongrass (*Sorghum halepense*), dallisgrass (*Paspalum dilatatum*), giant foxtail (*Setaria faberii*), cheatgrass (*Bromus secalinus*), mustard (*Brassica arvensis*), cocklebur (*Xanthium pennsylvanicum*), pigweed (*Amaranthus retroflexus*), morningglory (*Ipomoea hederacea*), cassia (*Cassia tora*), teaweed (*Sida spinosa*), velvetleaf (*Abutilon theophrasti*), and jimsonweed (*Datura stramonium*). A 12.5 cm diameter plastic pot was also filled with prepared soil and planted with rice and wheat. Another 12.5 cm pot was planted with sugarbeets. The above four containers were treated pre-emergence with several test compounds within the scope of the invention.

Twenty-eight days after treatment, the plants were evaluated and visually rated for response to the chemical treatments utilizing the rating system described previously for Test A. The data are summarized in Table XVI.

TABLE XVI

| Structure | Rate kg/ha | Crab-grass | Barnyard-grass | Sorghum | Wild Oats | Johnsongrass | Dallisgrass | Giant Foxtail | Ky. bluegrass | Cheat-grass | Corn | Mus-tard | Cockle-bur |
|---|---|---|---|---|---|---|---|---|---|---|---|---|---|
|  | .25 | 0 | 0 | 0 | 0 | 0 | 0 | 0 | 0 | 0 | 0 | 8G | 10C |
|  | .25<br>.063 | 8G,8H<br>5G | 7G,3H<br>3G | 8G,5H<br>6G,3H | 4G<br>0 | 3H,5G<br>0 | 10C<br>0 | 5G,3H<br>3G,3H | 5G<br>0 | 8G,8C<br>3G | 6G,3H<br>3G | 3G<br>0 | 0<br>0 |
| 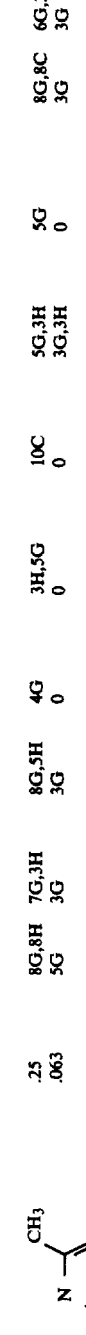 | .25 | 0 | 0 | 2G | 0 | 0 | 0 | 3H | 2H | 2H | 3G | | |

PRE-EMERGENCE ON FALLSINGTON SILT LOAM

| Structure | Rate kg/ha | Crab-grass | Barnyard-grass | Sorghum | Wild Oats | Johnsongrass | Dallisgrass | Giant Foxtail | Ky. bluegrass | Cheat-grass | Sugar-beets | Corn | Mus-tard |
|---|---|---|---|---|---|---|---|---|---|---|---|---|---|
| <br>m.p. 210–215° | 0.06<br>0.25 | 0<br>0 | 3G<br>5G | 0<br>3G | 0<br>0 | 7G,5H<br>9G,5H | 4G<br>6G | 3G<br>7G,5H | 6G<br>9G,9C | 4G<br>9G,8C | 6G<br>9G,9C | 3G<br>9G,9H | 9G,9C<br>10C |
| m.p. 204–213° | 0.03<br>0.12 | 0<br>0 | 0<br>0 | 0<br>0 | | 0<br>3G | 0<br>0 | 0<br>0 | 0<br>5G | 0<br>3G | 0<br>3G | 0<br>0 | 0<br>8G,3C |

TABLE XVI-continued

| | Rate kg/ha | Pigweed | Nutsedge | Morningglory | Cassia | Teaweed | Velvetleaf | Jimsonweed | Soybean | Rice | Wheat | Sugarbeets |
|---|---|---|---|---|---|---|---|---|---|---|---|---|
| Structure 1: 2-amino-toluene with SO₂NHCNH linked to pyrimidine (OCH₃, CH₃), m.p. 132-135° | 0.03<br>0.12 | 0<br>0 | 0<br>3G | 0<br>0 | 0<br>0 | 0<br>0 | 0<br>0 | 0<br>4G | 0<br>0 | 0<br>0 | 0<br>0 | 0<br>0 |
| Structure 2: 2-amino-toluene with SO₂NHCNH linked to triazine (OCH₃, OCH₃), m.p. 205-212° | 0.03<br>0.12 | 0<br>3G | 0<br>3G | 0<br>0 | 0<br>3G | 0<br>0 | 0<br>0 | 0<br>0 | 3G<br>3G | 0<br>0 | 0<br>0 | 0<br>0 | 0<br>6G |
| Structure 3: disubstituted benzene with two SO₂NHCNH groups, m.p. 216-218° | 0.03<br>0.12 | 0<br>2G | 0<br>0 | 0<br>3G | 0<br>0 | 0<br>3G | — <br>— | 0<br>0 | 4G<br>3G | — <br>— | 0<br>0 | 0<br>0 | 0<br>5G,3H |
| Structure 4: 2-amino-toluene with SO₂NHCNH linked to pyrimidine (OCH₃, OCH₃), m.p. 104-106° | 0.03 | 0 | 0 | 0 | 0 | 0 | 0 | 0 | 0 | 0 | 0 | 0 | 3G |
| Structure 5: pyrimidine (CH₃, OCH₃) linked via SO₂NHCNH to benzene with NH—CO—CH(CH₃)₂ | .25 | 8G | 0 | 0 | 0 | 0 | 0 | 0 | 0 | 0 | 0 | 0 | 0 |

TABLE XVI-continued

| Structure | Rate kg/ha | Cocklebur | Pigweed | Nutsedge | Cotton | Morningglory | Cassia | Teaweed | Velvetleaf | Jimsonweed | Soybean | Rice | Wheat |
|---|---|---|---|---|---|---|---|---|---|---|---|---|---|
| [structure with CH₃, OCH₃, pyrimidine, SO₂NHCNH, NH—C—OCH₃] | .25<br>.063 | 0<br>5G | 10E<br>10E | 10E<br>0 | 2G<br>0 | 0<br>0 | 5G<br>7G | 5G<br>8G | 0<br>3C | 3G<br>7G | 5G<br>7G | 8G,9G<br>5G | 6G<br>0 | 3G<br>0 |
| [structure with CH₃, OCH₃, pyrimidine, SO₂NHCNH, NCO] | .25 | 0 | 0 | 0 | 0 | 0 | 0 | 0 | 0 | 0 | 0 | 0 | 0 | 0 |

PRE-EMERGENCE ON FALLSINGSTON SILT LOAM

| Structure | Rate kg/ha | Cocklebur | Pigweed | Nutsedge | Cotton | Morningglory | Cassia | Teaweed | Velvetleaf | Jimsonweed | Soybean | Rice | Wheat |
|---|---|---|---|---|---|---|---|---|---|---|---|---|---|
| [structure with OCH₃, CH₃, pyrimidine, SO₂NHCNH, NH₂ on phenyl] m.p. 210–215° | 0.06<br>0.25 | 0<br>0 | 3G<br>8G,5C | 0<br>0 | 0<br>3G | 0<br>2G | 0<br>2G | 0<br>0 | 0<br>0 | 0<br>0 | 4G<br>6G,3H | 6H<br>9H | 0<br>5G |
| [structure with OCH₃, CH₃, pyrimidine, CH₃, SO₂NHCNH, H₂N on phenyl] m.p. 204–213° | 0.03<br>0.12 | 0<br>0 | 0<br>6G | 0<br>0 | 0<br>0 | 0<br>0 | 0<br>0 | 0<br>0 | 0<br>0 | 0<br>0 | 0<br>0 | 3G<br>7G,5H | 0<br>4G |
| [structure with OCH₃, CH₃, pyrimidine, CH₃, SO₂NHCNH, H₂N on phenyl] m.p. 132–135° | 0.03<br>0.12 | 0<br>0 | 0<br>0 | 0<br>0 | 0<br>0 | 0<br>0 | 0<br>0 | 0<br>0 | 0<br>0 | 0<br>0 | 0<br>0 | 0<br>0 | 0<br>0 |

TABLE XVI-continued

| Structure | | | | | | | | | | | |
|---|---|---|---|---|---|---|---|---|---|---|---|
| ![structure with m.p. 205-212°] | 0.03 | 0 | 0 | 0 | 0 | 0 | 0 | 0 | 0 | 0 | 0 |
| | 0.12 | 0 | 4G | 0 | 0 | 3G | 0 | 0 | 0 | 3G | 0 |
| | | | | | | | | | | 6G | 0 |
| ![structure with m.p. 216-218°] | 0.03 | 0 | 5G | 0 | 0 | 0 | 0 | 0 | 0 | 0 | 0 |
| | 0.12 | 0 | 7G | 0 | — | 0 | 0 | 0 | 2G | 3G | 0 |
| ![structure with m.p. 104-106°] | 0.03 | 0 | 0 | 0 | 0 | 0 | 0 | 0 | 0 | 0 | 0 |

Test D

Compounds were applied to both black valentine ("pole" type) and tendercrop beans ("bush" type). The treatment was applied in a suitable nonphytotoxic solvent when the black valentine beans had the first trifoliolate leaf and the developing tendercrop beans were in the early flower bud stage. Treated plants and controls were maintained in a greenhouse and response ratings taken 1 and 4 weeks after treatment. Pod yields were taken between 3 and 4 weeks after treatment. Yield results are recorded as a percentage of untreated controls. Ratings for compounds tested by this procedure are recorded in Table XVII.

TABLE XVII

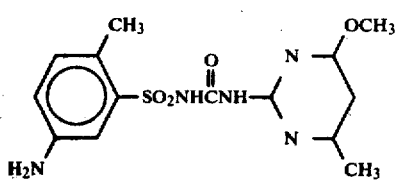

| | POLE BEAN | | BUSH BEAN | | | |
|---|---|---|---|---|---|---|
| Kg/Ha | 1 Week | 4 Weeks | 1 Week | 4 Weeks | No. Fruit | Fruit Weight |
| .031 | 3C | 6C | 3C | 3C | 0 | 0 |
|  | 5G | 7G | 3G | 3G |  |  |
| .125 | 5C | 8C | 5C | 7C | 0 | 0 |
|  | 6G | 7G | 4G | 4G |  |  |
| .5 | 4H | 9C | 5H | 9C | 0 | 0 |
|  | 7C | 9G | 7C | 8G |  |  |
|  | 9G |  |  | 8G |  |  |

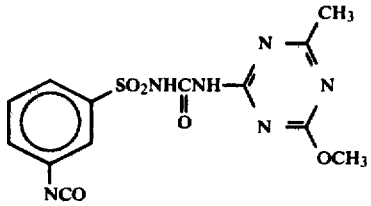

| | POLE BEAN | | BUSH BEAN | | | |
|---|---|---|---|---|---|---|
| Kg/Ha | 1 Week | 4 Weeks | 1 Week | 4 Weeks | No. Fruit | Fruit Weight |
| .125 | 3C | 4C | 4C | 3G | 2 | 0 |
|  | 4G | 5G | 3G | 3C |  |  |
|  |  |  |  | 2H |  |  |
| .5 | 6C | 8C | 6C | 7C | 0 | 0 |
|  | 7G | 8G | 5G | 7G |  |  |
| 2.0 | 7C | 10C | 7C | 6C | 0 | 0 |
|  | 8G |  |  | 7G |  |  |
|  |  |  |  | 4H |  |  |
|  |  |  |  | 6G |  |  |

Test E

Purple nutsedge (*Cyperus rotundus*) tubers were planted about 2 cm deep in Fallsington silt loam soil contained in 10 cm diameter plastic pots. Five tubers were planted in each pot. Compounds of this invention were dissolved in a non-phytotoxic diluent and sprayed at 560 l/ha in four methods of application: soil surface, tuber/soil, soil incorporated and post-emergence. The soil surface spray consisted of spraying the compound on the surface of the firmed covering soil. The tuber/soil spray consisted of spraying the compound on exposed tubers and subtending soil before adding the untreated covering soil. Soil incorporated treatment consisted in mixing the compound with the covering soil before using it to cover the tubers. The post-emergence treatment was sprayed on nutsedge foliage and the surrounding soil surface when nutsedge had emerged and grown to a height of about 12 cm. Pots receiving the post-emergence treatments were placed directly in the greenhouse. Pots receiving the other treatments were misted with about 0.3 cm water before being transferred to the greenhouse. Response ratings assessed after four weeks are recorded in Table XVIII based on the same rating system as described in procedure A.

Perennial Grass Screen
Nutsedge Control

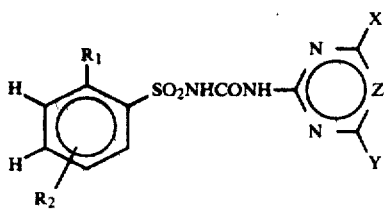

| | Response Rating (After 4 Weeks) | | | |
|---|---|---|---|---|
| Rate kg/ha | Preemerg. Soil Surface | Tuber Spray | Soil Incorp. | Postemerg. |
| .125 | 0 | 0 | 0 | 0 |
| .5 | 8E,9G | 8E,8G | 10E | 7C |

TABLE XVIII $$\underset{NCO}{\text{[structure]}}\text{—SO}_2\text{NHCNH—[pyrimidine with CH}_3\text{, OCH}_3\text{]}$$

PLANT RESPONSE 4 WEEKS AFTER TREATMENT

| Rate, kg/ha | Pre surface spray | Pre tuber + soil spray | Pre soil inc. 2.5 cm. | Post foliar spray |
|---|---|---|---|---|
| 2.0 | 3E | 3C | 3C | 4W |
|  | 8C | 7G | 8G | 3G |
| 0.5 | 0 | 2G | 2G | 0 |

What is claimed is:

1. A compound selected from $$\text{(I)}$$

wherein
$R_1$ is H, Cl, Br, F, $CH_3$, $OCH_3$ or $NO_2$;
$R_2$ is $-NHCOSR_3$, $-NHCOR_3$, or $-NR_6R_7$;
$R_3$ is alkyl of 1–4 carbon atoms;
$R_6$ is H or alkyl of 1–3 carbon atoms;
$R_7$ is H or alkyl of 1–3 carbon atoms; or
$R_6$ and $R_7$ taken together are $-(CH_2)_n-$ or $-CH_2CH_2OCH_2CH_2-$;
n is 4 or 5;

X is methyl, methoxy or ethoxy;
Y is methyl or methoxy; and
Z is N;
provided that:
(a) when $R_2$ is ortho to the sulfonylureido group, then $R_1$ must be hydrogen.

2. A compound of claim 1 wherein
$R_2$ is $-NR_6R_7$, or $-NHCOCH_3$; and
$R_6$ and $R_7$ are independently hydrogen or alkyl of 1–3 carbon atoms.

3. A compound of claim 2 wherein
$R_2$ is $-NR_6R_7$;
$R_6$ and $R_7$ are independently hydrogen or methyl; and
X is methyl or methoxy.

4. A compound of claim 2 or 3 wherein
$R_1$ is hydrogen, chlorine, methyl or methoxy.

5. The compound of claim 1, 5-amino-N-[(4-methoxy-6-methyl-1,3,5-triazin-2-yl)aminocarbonyl]-2-methylbenzenesulfonamide.

6. The compound of claim 1, 5-amino-N-[(4,6-dimethoxy-1,3,5-triazin-2-yl)aminocarbonyl]-2-methylbenzenesulfonamide.

7. The compound of claim 1, 2-amino-N-[(4-methoxy-6-methyl-1,3,5-triazin-2-yl)aminocarbonyl]benzenesulfonamide.

8. A composition for the control of undesirable vegetation consisting essentially of a compound of claim 1 and at least one of (a) a surface-active agent and (b) a solid or liquid diluent.

9. A composition for the control of undesirable vegetation consisting essentially of a compound of claim 2 and at least one of (a) a surface-active agent and (b) a solid or liquid diluent.

10. A composition for the control of undesirable vegetation consisting essentially of a compound of claim 3 and at least one of (a) a surface-active agent and (b) a solid or liquid diluent.

11. A composition for the control of undesirable vegetation consisting essentially of the compound of claim 4 and at least one of (a) a surface-active agent and (b) a solid or liquid diluent.

12. A method for the control of undesirable vegetation comprising applying to the locus of such undesirable vegetation a herbicidally effective amount of a compound of claim 1.

13. A method for the control of undesirable vegetation comprising applying to the locus of such undesirable vegetation a herbicidally effective amount of a compound of claim 2.

14. A method for the control of undesirable vegetation comprising applying to the locus of such undesirable vegetation a herbicidally effective amount of a compound of claim 3.

15. A method for the control of undesirable vegetation comprising applying to the locus of such undesirable vegetation a herbicidally effective amount of a compound of claim 4.

16. A compound of claim 1 where $R_1$ is H, Cl, Br, F, $CH_3$, $OCH_3$ or $NO_2$.

17. A composition for the control of undesirable vegetation consisting essentially of a compound of claim 16 and at least one of (a) a surface-active agent and (b) a solid or liquid diluent.

18. A method for the control of undesirable vegetation comprising applying to the locus of such undesirable vegetation a herbicidally effective amount of a compound of claim 16.

* * * * *